(12) United States Patent
Reardon

(10) Patent No.: US 9,499,853 B2
(45) Date of Patent: Nov. 22, 2016

(54) BIOSENSING SYSTEM WITH EXTENDED LIFETIME VIA COFACTOR RECYCLING

(75) Inventor: Kenneth F. Reardon, Fort Collins, CO (US)

(73) Assignee: COLORADO STATE UNIVERSITY RESEARCH FOUNDATION, Fort Collins, CO (US)

(*) Notice: Subject to any disclaimer, the term of this patent is extended or adjusted under 35 U.S.C. 154(b) by 0 days.

(21) Appl. No.: 14/236,531

(22) PCT Filed: Aug. 2, 2012

(86) PCT No.: PCT/US2012/049384
§ 371 (c)(1),
(2), (4) Date: Jan. 31, 2014

(87) PCT Pub. No.: WO2013/019982
PCT Pub. Date: Feb. 7, 2013

(65) Prior Publication Data
US 2014/0154724 A1 Jun. 5, 2014

Related U.S. Application Data

(63) Continuation-in-part of application No. 13/562,592, filed on Jul. 31, 2012.

(60) Provisional application No. 61/514,309, filed on Aug. 2, 2011.

(51) Int. Cl.
*C12N 9/02* (2006.01)
*C12N 11/00* (2006.01)
*C12Q 1/26* (2006.01)
*C12Q 1/32* (2006.01)
(Continued)

(52) U.S. Cl.
CPC ............ *C12Q 1/26* (2013.01); *C12N 9/0004* (2013.01); *C12N 9/0069* (2013.01); *C12N 9/0071* (2013.01); *C12Q 1/32* (2013.01); *C12Y 102/01002* (2013.01); *C12Y 114/13* (2013.01); *C12Y 113/00* (2013.01); *C12Y 114/00* (2013.01)

(58) Field of Classification Search
None
See application file for complete search history.

(56) References Cited

U.S. PATENT DOCUMENTS

| 4,739,380 A | 4/1988 | Lauks et al. |
| 5,141,312 A | 8/1992 | Thompson et al. |
| 5,152,758 A | 10/1992 | Kaetsu et al. |

(Continued)

FOREIGN PATENT DOCUMENTS

| EP | 1369687 | 12/2003 |
| EP | 1369687 A1 | 12/2003 |

(Continued)

OTHER PUBLICATIONS

Hollman, F; Schmid, A; Steckhan, E "The First Synthetic Application of a Monooxygenase Employing Indirect Electrochemical NADH Regeneration" Angew. Chem Int. Ed., 2001, 40(1), pp. 169-171.*

(Continued)

*Primary Examiner* — Louise W Humphrey
*Assistant Examiner* — Aaron J Kosar
(74) *Attorney, Agent, or Firm* — Faegre Baker Daniels LLP

(57) ABSTRACT

The present disclosure relates to biosensing systems and biosensing elements having increased storage capability and increased functional lifetimes through using compositions and methods for recycling cofactors.

19 Claims, 7 Drawing Sheets

(51) Int. Cl.
G01N 21/77 (2006.01)
C12M 1/34 (2006.01)

(56) References Cited

U.S. PATENT DOCUMENTS

| | | | |
|---|---|---|---|
| 5,156,810 A | 10/1992 | Ribi | |
| 5,177,012 A | 1/1993 | Kim et al. | |
| 5,250,439 A | 10/1993 | Musho et al. | |
| 5,340,722 A | 8/1994 | Wolfbeis et al. | |
| 5,508,193 A | 4/1996 | Mandelbaum et al. | |
| 5,541,057 A | 7/1996 | Bogart et al. | |
| 5,543,317 A | 8/1996 | Shields et al. | |
| 5,580,527 A | 12/1996 | Bell et al. | |
| 5,629,214 A | 5/1997 | Crosby | |
| 5,698,083 A | 12/1997 | Glass | |
| 5,798,030 A | 8/1998 | Raguse et al. | |
| 5,837,196 A | 11/1998 | Pinkel et al. | |
| 5,837,454 A | 11/1998 | Cozzette et al. | |
| 5,853,669 A | 12/1998 | Wolfbeis | |
| 5,972,199 A | 10/1999 | Heller et al. | |
| 5,972,638 A | 10/1999 | Burlage et al. | |
| 6,022,748 A | 2/2000 | Charych et al. | |
| 6,060,327 A | 5/2000 | Keen | |
| 6,100,080 A | 8/2000 | Johansen | |
| 6,136,979 A * | 10/2000 | Hudlicky et al. | 546/62 |
| 6,159,681 A | 12/2000 | Zebala | |
| 6,265,201 B1 | 7/2001 | Wackett et al. | |
| 6,271,015 B1 | 8/2001 | Gilula et al. | |
| 6,284,522 B1 | 9/2001 | Wackett et al. | |
| 6,291,200 B1 | 9/2001 | LeJeune et al. | |
| 6,369,299 B1 | 4/2002 | Sadowsky et al. | |
| 6,576,449 B2 * | 6/2003 | Clark et al. | 435/132 |
| 6,592,746 B1 | 7/2003 | Schmid-Schoenbein et al. | |
| 6,825,001 B2 | 11/2004 | Wackett et al. | |
| 7,595,181 B2 | 9/2009 | Grüning et al. | |
| 7,709,221 B2 | 5/2010 | Rose et al. | |
| 2002/0168733 A1* | 11/2002 | Clark et al. | 435/124 |
| 2003/0207345 A1* | 11/2003 | Arnold et al. | 435/25 |
| 2004/0265811 A1 | 12/2004 | Reardon et al. | |
| 2005/0084921 A1 | 4/2005 | Cranley et al. | |
| 2005/0221276 A1 | 10/2005 | Rozakis et al. | |
| 2006/0275855 A1 | 12/2006 | Blackburn et al. | |
| 2009/0026092 A1* | 1/2009 | Reardon et al. | 205/778 |
| 2009/0221014 A1 | 9/2009 | Reardon et al. | |
| 2010/0116691 A1 | 5/2010 | Papadimitrakopoulos et al. | |

FOREIGN PATENT DOCUMENTS

| | | |
|---|---|---|
| EP | 1369687 A1 | 12/2003 |
| WO | WO 93/25892 | 12/1993 |
| WO | WO9325892 A1 | 12/1993 |

OTHER PUBLICATIONS

Zakhari, S "Overview: How Is Alcohol Metabolized by the Body?" NIH-NIAAA, archived online May 27, 2010, 12 pages.*
Adachi, K., et al; Purification and properties of homogentisate oxygenase from *Pseudomonas fluorescens*. Biochim. Biophys. Acta 118 (1966) 88-97.
Amitai, G. et al.; Enhanced stereoselective hydrolysis of toxic organophosphates by directly evolved variants of mammalian serum paraoxonase; FEBS Journal 273 (2006) pp. 1906-1919.
Augusteyn, R.C., et al; On the homology of the active-site peptides of liver Carboxylesterases. Biochim. Biophys. Acta 171 (1969) 128-137.
Augustinsson, K.-B. and Heimburger, G. Enzymatic hydrolysis of organophosphorus compounds. I. Occurrence of enzymes hydrolysing dimethyl-amido-ethoxy-phosphoryl cyanide (Tabun). Acta Chem. Scand. 8 (1954) 753-761.
Bertoni, G., et al; "Analysis of the Gene Cluster Encoding Toluene/ o-Xylene Monoxygenase from *Pseudomonas stutzeri* OX1," Applied and Environmental Microbiology, 1998. 64(10): pp. 3626-3632.
Buchinger, P.J. et al.; Characteristics of Microbial Assay for the Detection of Halogenated Hydrocarbons Using Cells of an Actinomycete-like Organism as a Biological Component; Acta Biotechnol. 17 (1997) 2, 123-130.
Cardini, G. & Jurtshuk, P. The enzymatic hydroxylation of n-octane by *Corynebacterium* sp. strain 7E1C. J. Biol. Chem. 245 (1970) 2789-2796.
Cardy, D.L.N., V. Laidler, G.P.C. Salmond, and J.C. Murrell, "Molecular Analysis of the Methane Monooxygenase (MMO) Gene Cluster of Methylosinus trichosporium OB3b," Molecular Microbiology, 1991. 5(2): pp. 335-342.
Chang, K. H., et al; Isolation and characterization of the three polypeptide components of 4-chlorobenzoate dehalogenase from *Pseudomonas* sp. strain CBS-3. Biochemistry 31 (1992) 5605-5610.
Chopra, I. J. & Teco, G. N. C. Characteristics of inner ring (3 or 5) monodeiodination of 3,5-diiodothyronine in rat liver: evidence suggesting marked similarities of inner and outer ring deiodinases for iodothyronines. Endocrinology 110 (1982) 89-97.
Colby, J. et al; The soluble methane mono-oxygenase of *Methylococcus capsulatus* (Bath). Its ability to oxygenate n-alkanes, n-alkenes, ethers, and alicyclic, aromatic and heterocyclic compounds. Biochem. J. 165 (1977) 395-402.
Crooks, G. P. & Copley, S. D.; Purification and characterization of 4-chlorobenzoyl CoA dehalogenase from *Arthrobacter* sp. strain 4-CB1. Biochemistry, 33 (1994) 11645-11649.
de Souza, M. L. et al; Cloning, characterization, and expression of a gene region from *Pseudomonas* sp. strain ADP involved in the dechlorination of atrazine. Appl. Environ. Microbiol. 61 (1995) 3373-3378.
de Souza, M. L., et al; Atrazine chlorohydrolase from *Pseudomonas* sp. strain ADP: gene sequence, enzyme purification, and protein characterization. J. Bacteriol. 178 (1996) 4894-4900.
Ensley, B.D. & Gibson, D.T. Naphthalene dioxygenase: purification and properties of a terminal oxygenase component. J. Bacteriol. 155 (1983) 505-511.
Fetzner, S., et al; Degradation of 2-chlorobenzoate by *Pseudomonas cepacia* 2CBS. Biol. Chem. Hoppe-Seyler 370 (1989) 1173-1182.
Fox, B.G., et al., "Methane Monooxygenase from Methylosinus trichosporium OB3b," Journal of Biological Chemistry, 1989. 264(17): pp. 10023-10033.
Fujisawa, H. & Hayaishi, O.; Protocatechuate 3,4-dioxygenase. I. Crystallization and characterization. J. Biol. Chem. 243 (1968) 2673-2681.
Goldman, P. & Milne, G. W. A.; Carbon-fluorine bond cleavage. II. Studies on the mechanism of the defluorination of fluoroacetate. J. Biol. Chem. 241 (1966) 5557-5559.
Goldman, P., et al.; Carbon-halogen bond cleavage. 3. Studies on bacterial halidohydrolases. J. Biol. Chem. 243 (1968) 428-434.
Goldman, P.; The enzymatic cleavage of the carbon-fluorine bond in fluoroacetate. J. Biol. Chem. 240 (1965) 3434-3438.
Goswami, A., et al.; Inhibition by coumadin anticoagulants of enzymatic outer ring monodeiodination of iodothyronines. Biochem. Biophys. Res. Commun. 104 (1982) 1231-1238.
Heppel, L. A. & Porterfield, V. T. Enzymatic dehalogenation of certain brominated and chlorinated compounds. *J. Biol. Chem.* 176 (1948) 763-769.
Hosokawa, K. & Stanier, R.Y. Crystallization and properties of p-hydroxybenzoate hydroxylase from *Pseudomonas putida*. J. Biol. Chem. 241 (1966) 2453-2460.
Junker, F., et al; Dioxygenation and spontaneous deamination of 2-aminobenzene sulphonic acid in *Alcaligenes* sp. strain O-1 with subsequent meta ring cleavage and spontaneous desulphonation to 2-hydroxymuconic acid. Biochem. J. 300 (1994) 429-436.
Keuning, S., Janssen, D. B. & Witholt, B.; Purification and characterization of hydrolytic haloalkane dehalogenase from Xanthobacter autotrophicus GJ10; J. Bacteriol. 163 (1985) 635-639.
Kohler-Staub, D. & Leisinger, T.; Dichloromethane dehalogenase of *Hyphomicrobium* sp. strain DM2. J. Bacteriol. 162 (1985) 676-681.
Kumagai, H., et al; S-Carboxymethylcysteine synthase from *Escherichia coli*. Agric. Biol. Chem. 53 (1989) 2481-2487.
Lipke, H. & Kearns, C. W.; DDT dechlorinase. I. Isolation, chemical properties, and spectrophotometric assay. J. Biol. Chem. 234 (1959) 2123-2128.

(56) References Cited

OTHER PUBLICATIONS

Lipke, H. & Kearns, C. W.; DDT dechlorinase. II. Substrate and cofactor specificity. J. Biol. Chem. 234 (1959) 2129-2132.

Moriguchi, M., et al.; Dehalogenation and deamination of 1-2-amino-4-chloro-4-pentenoic acid by *Proteus mirabilis*. Agric. Biol. Chem. 51 (1987) 3295.

Motosugi, M., et al.; Preparation and properties of 2-halo acid dehalogenase from *Pseudomonas putida*. Agric. Biol. Chem. 46 (1982) 837-838.

Mulchandani, A. et al.; Biosensor for Direct Determination of Organophosphate Nerve Agents Using Recombatant *Escherichia coli* with Surface-Expressed Organophosphorus Hydrolase.—2. Fiber-Optic Microbial Bionsenor; ., Analytical Chemistry 1998 70 (23), 5042-5046.

Muller, C. et al.; Multicomponent fiberoptical biosensor for use in hemodialysis monitoring; SPIE Biomedical Fiber Optic Instrumentation; vol. 2131; pp. 555-562 (Jul. 1994).

Muller, R., et al.; Incorporation of [18O] water into 4-hydroxybenzoic acid in the reaction of 4-chlorobenzoate dehalogenase from *Pseudomonas* sp. CBS 3. Biochem. Biophys. Res. Commun. 124 (1984) 178-182.

Nagasawa, T.,et al.; Physiological comparison of D-cysteine desulfhydrase of *Escherichia coli* with 3-chloro-D-alanine dehydrochlorinase of *Pseudomonas putida* CR 1-1. Arch. Microbiol. 149 (1988) 413-416.

Nordlund, I., et al, "Complete nucleotide sequence and polypeptide analysis of multicomponent phenol hydroxylase from *Pseudomonas* strain CF600," Journal of Bacteriology, 1990. 172: pp. 6826-6833.

PCT/US2002/017407 International Search Report; mailed Sep. 24, 2003; 2 pages.

PCT/US2009/040121, International Search Report & Written Opinion mailed Jul. 14, 2009, 7 Pages.

Renganathan, V. Possible involvement of toluene-2,3-dioxygenase in defluorination of 3-fluoro-substituted benzenes by toluene-degrading *Pseudomonas* sp. strain T-12. Appl. Exp. Microbiol. 55 (1989) 330-334.

Rosenzwieg, A.C., et al. "Geometry of the Soluble Methane Monoxygenase Catalytic Diiron Center in Two Oxidation States," Chemistry and Biology, 1995. 2(6): pp. 409-418.

Schenk, T., et al.; Enzymatic dehalogenation of pentachlorophenol by extracts from *Arthrobacter* sp. strain ATCC 33790. J. Bacteriol. 171 (1989) 5487-5491.

Scholtz, R., et al.; Characterization of 1-chlorohexane halidohydrolase, a dehalogenase of wide substrate range from an *Arthrobacter* sp. J. Bacteriol. 169 (1987) 5016-5021.

Smallridge, R. C., et al. "3',5'-Diiodothyronine to 3'-monoiodothyronine conversion in the fed and fasted rat: enzyme characteristics and evidence for two distinct 5'-deiodinases" Endocrinology 108 (1981) 2336-2345.

Stainthorpe, A.C., et al., "The Methane Monooxygenase Gene Cluster of *Methylococcus capsulatus* (Bath)," Gene, 1990. 91: pp. 27-34.

Suzuki, K., Takemori, S. and Katagiri, M. Mechanism of the salicylate hydroxylase reaction. IV. Fluorimetric analysis of the complex formation. Biochim. Biophys. Acta 191 (1969) 77-85.

Yamada, H., et al; Synthesis of D-cysteine from 3- chloro-D-alanine and hydrogen sulfide by 3-chloro-D-alanine hydrogen chloride-lyase (deaminating) of *Pseudomonas putida*. Biochem. Biophys. Res. Commun. 100 (1981) 1104-1110.

Yen, K.-M., "Construction of Cloning Cartridges for Development of Expression Vectors in Gram-Negative Bacteria," J. Bacteriol., 1991. 173(17): pp. 5328-5335.

Yokota, T., et al.; Purification and properties of haloalkane dehalogenase from *Corynebacterium* sp. strain m15-3. J. Bacteriol. 169 (1987) 4049-4054.

Conzuelo, F. et al., An Integrated amperometric biosensor for the determination of lactose in milk and dairy products, J. Agric. Food Chern., Jun. 23, 2010, pp. 7141-7148.

Plata, M.R. et al., State-of-the-art of (bio)chemical sensor developments in analytical spanish groups, Sensors, Mar. 24, 2010, pp. 2511-2576.

PCT/US11/61956 International Search Report and Written Opinion mailed Jun. 14, 2012, 10 pages.

PCT/US12/49384 International Search Report and Written Opinion mailed Feb. 20, 2012, 11 pages.

PCT/US12/58331 International Search Report and Written Opinion mailed Mar. 29, 2013, 11 pages.

PCT/US02/17407, International Preliminary Examination Report, Mar. 5, 2005, 4 pages.

Zhong, Z. et al., Fiber optic monooxygenase biosensor for toluene concentration measurement in aqueous samples, Biosensors and Bioelectronics 26 (2011) 2407-2412.

U.S. Appl. No. 10/478,822.

U.S. Appl. No. 12/100,308.

U.S. Appl. No. 12/358,140.

Posch, H.E. & Wolfbeis. O.S., Optical sensor for hydrogen peroxide. Microchimica Acta 97 (1989) 41-50.

Rajendran, V., Lrudayaraj, J. Detection of glucose, galactose, and lactose in milk with a microdialysis-coupled flow injection amperometric sensor. J Dairy Sci. 85 (2002) 1357-61.

Pilloton, R et al., Lactose Determination in Raw Milk with a Two-Enzyme Based Electrochemical Sensor. Analytical Letters. 20 (1987) 1803-1814.

Tkác J, et al., Novel glucose non-interference biosensor for lactose detection based on galactose oxidase-peroxidase with and without co-immobilised beta-galactosidase. Analyst. 125 (2000) 1285-9.

Wichmann, R. & Vasic-Racki. D.; Cofactor Regeneration at the Lab Scale. Adv Biochem Engin/Biotechnol 92 (2005) 225-260.

Zhao, H. & van der Donk, W.A.. Regeneration of cofactors for use in biocatalysis. Current Opinion in Biotechnology. 14 (2003) 583-589.

Woodyer, R.D. et al. (2005) Regeneration of cofactors for enzyme biocatalysis. Enzyme Technology, 85-103.

Johannes, T.W. et al. (2005). Directed evolution of a thermostable phosphite dehydrogenase for NAD(P)H regeneration. Applied and Environmental Microbiology, 71(10), 5728-5734. doi:10.1128/AEM.71.10.5728-5734.2005.

Snaked, Z. & Whitesides, G.M., Enzyme-catalyzed organic synthesis: NADH regeneration by using formate dehydrogenase. J. Am. Chem. Soc. 102 (1980) 7104-7105.

Berríos-Rivera, .S.J. et al. Metabolic engineering of *Escherichia coli*: increase of NADH availability by overexpressing an NAD(+)-dependent formate dehydrogenase. Metab Eng. 4 (2002) 217-29.

PCT/US2012/049384, International Search Report and Written Opinion mailed Feb. 20, 2013, 11 pages.

U.S. Appl. No. 12/100,308, Office Action mailed Apr. 6, 2015; 9 pages.

U.S. Appl. No. 14/348,426, Office Action mailed Apr. 2, 2015; 19 pages.

Carswell et al. "An Optical Oxygen Sensor Based on Rudpp Fluorescent Quenching," SPIE vol. 2705, Mar. 1996, pp. 22-30.

Lee et al. "Proteome Changes after Metabolic Engineering to Enhance Aerobic Mineralization of cis-1, 2-Dichloreothylene," Journal of Proteome Research, 2006, pp. 1388-1397. American Chemical Society, Web.

Mars et al. "Effect of Trichloreothylene on Competitive Behavior of Toluene-Degrading Bacteria," Applied and Environmental Microbiology, 1998, vol. 64 (1), pp. 208-215.

Neujahr, Halina, "Determination of Phenol and Catechol Concentrations with Oxygen Probes Coated with Immobilized Enzymes or Immobilized Cells," Applied Biochemistry and Biotechnology, 1982, vol. 7, pp. 107-111.

Rui et al. "Metabolic pathway engineering to enhance aerobic degradation of chlorinated ethenes and to reduce their toxicity by cloning a novel glutathione S-transferase, an evolved toluene o-monooxygenase, and y-glutamylcysteine synthetase," Environmental Microbiology, 2004, 6(5), pp. 491-500.

Stokes et al. "An optical oxygen sensor and reaction vessel for high-pressure applications," Limnol. Ocearnogr., 1999, vol. 44(1 ):189-195.

(56) References Cited

OTHER PUBLICATIONS

Sundari et al. "Retention of enzyme activity following freeze-drying the mycelium of ectomycorrhizal isolates: part II. Enzymes acting upon carbon compounds" World Journal of Microbiology and Biotechnology, 2000, vol. 16, pp. 865-868.
Zhong, Z. "Fiber Optic Enzymatic Biosensors and Biosensor Arrays for Measurement of Chlorinated Ethenes," Dissertation, Colorado State University, (submission date Apr. 2, 2011), 158 Pages, published Aug. 21, 2011.
U.S. Appl. No. 13/562,592 Non-Final Rejection dated Oct. 8, 2015, 20 pages.
Adachi, K., et al; Purification and properties of homogentisate oxygenase from Pseudomonas fluorescens. Biochim. Biophys. Acta 118(1966) 88-97.
Aldridge, W.N.; Serum esterases. I. Two types of esterase (A and B) hydrolysing p-nitrophenyl acetate, propionate and butyrate and a method for their determination. Biochem. J. 53 (1953) 110-117.
Amitai, G. et al.; Enhanced stereoselective hydrolysis of toxic organophosphat by directly evolved variants of mammalian serum paraoxonase; FEBS Journal273 (2006) pp. 1906-1919.
U.S. Appl. No. 10/478,822, selected pages from image file wrapper dated Jan. 12, 2007 through May 14, 2008, 126 pages.
U.S. Appl. No. 12/100,308, selected pages from image file wrapper dated Sep. 17, 2010 through Nov. 14, 2011, 118 pages.
U.S. Appl. No. 12/358,140, selected pages from image file wrapper dated Apr. 1, 2011 through Nov. 14, 2012, 77 pages.
Augusteyn, R.C., et al; On the homology of the active-site peptides of liver Carboxlesterases. Biochim. Biophys. Acta 171 (1969) 128-137.
Augustinsson, K.-B. and Heimburger, G. Enzymatic hydrolysis of organophosphorus compounds. I. Occurence of enzymes hydrolysing dimethyl-amido-ethoxy-phosphoryl cyanide (Tabun). Acta Chem. Scand. 8 (1954) 753-761.
Berrios-Rivera, .S.J. et al. Metabolic engineering of Escheria coli: increase of NADH availability by overexpressing an NAD(+)-dependent formate dehydrogenase. Metab Eng. 4 (2002) 217-29.
Bertoni, G., et al; "Analysis of the Gene Cluster Encoding Toluene/a-Xylene Monoxygenase from Pseudomonas stutzeri OX1,"Applied and Environmental Microbiology, 1998. 64(10): pp. 3626-3632.
Bertoni, G., et al; "Cloning of the Genes for and Characterization of the Early Stages of Toluene and o-Xylene Catabolism in Pseudomonas stutzeri OX1," Applied and Environmental Microbiology, 1996, 62(10): pp. 3704-3711.
Buchinger, P.J. et al.; Characteristics of Microbial Assay for the Detection of Halogenated Hydrocarbons Using Cells of an Actinomycete-like Organism as a Biological Component; Acta Biotechnol. 17 (1997)2, 123-130.
Byrne, A.M., et al; "Sequence Analysis of the Gene Cluster Encoding Toluene-3-monooxygenase from Pseudomonas pickettii PK01," Gene, 1995. 154: pp. 65-70.
Cardini, G. & Jurtshuk, P. The enzymatic hydroxylation of n-octane by Corynebacterium sp. Strain 7E1C. J. Bioi. Chern. 245 (1970) 2789-2796.
Cardy, D.L.N., V. Laidler, G.P.C. Salmond, and J.C. Murrell, "Molecular Analysis of the Methane Monooxygenase (MIMO) Gene Cluster of Methylosinius trichosporium OB3b," Molecular Microbiology, 1991. 5(2): pp. 335-342.
Carswell et al. "An Optical Oxygen Sensor Based on RUDPP Flourescent Quenching," SPIE vol. 2705, Mar. 25, 1996, pp. 22-30.
Chang, K. H., et al: Isolation and characterization of the three polypeptide components of 4-chlorobenzoate dehalogenase from Pseudomonas sp. strain CBS-3. Biochemistry 31 (1992) 5605-5610.
Chopra, I. J. & Teco, G. N. C. Characteristics of inner ring (3 or 5) monodeiodination of 3,5-diiodothyronine in rat liver: evidence suggesting marked similarities of inner and outer ring deiondinases for iodothyronines. Endocrinology 110 (1982) 89-97.

Colby, J. et al; The soluble methane mono-oxygenase of Methylococcus capsulatus (Bath). Its ability to oxygenate n-alkanes, n-alkenes, ethers, and alicyclic, aromatic and heterocyclic compounds. Biochem. J. 165-(1977) 395-402.
Conzuelo, F. et al., An Integrated amperometric biosensor for the determination of lactose in milk and dairy products, J. Agric. Food Chem., Jun. 23, 2010; pp. 7141-7148.
Crooks, G. P. & Copley, S. D.; Purification and characterization of 4-chlorobenzoyl GoA dehalogenase from Arthrobacter sp. strain 4-CB1. Biochemistry, 33 (1994) 11645-11649.
de Souza, M. L. et al; Cloning, characterization, and expression of a gene region from Pseudomonas sp. strain ADP involved in the dechlorination of atrazine. Appl. Environ. Microbial. 61 (1995) 3373-3378.
de Souza, M. L., et al; Atrazine chlorohydrolase from Pseudomonas sp. strain ADP: gene sequence, enzyme purification, and protein characterization. J. Bacterial. 178 (1996) 4894-4900.
Dodgson, K.S., et al; Studies on sulphatases. 13. The hydrolysis of substituted phenyl sulphates by the arylsulphatase of Alcaligenes metacaligenes. Biochem. J. 64 (1956) 216-221.
Ensley, B.D. & Gibson, D.T. Naphthalene dioxygenase: purification and properties of a terminal oxygenase component. J. Bacterial. 155 (1983) 505-511.
Fetzner, S., et al; Degradation of 2-chlorobenzoate by Pseudomonas cepacia 2CBS. Bioi. Chem. Hoppe-Seyler 370 (1989) 1173-1182.
Fox, B. G., et al., "Methane Monooxygenase from Methylosinus trichosporium OB3b," Journal of Biological Chemistry, 1989. 264(17): pp. 10023-10033.
Fujisawa, H. & Hayaishi, o.; Protocatechuate 3,4-dioxygenase. I. Crystallization and characterization. J. Bioi. Chem. 243 (1968) 2673-2681.
Goldman, P. & Milne, G. W. A.; Carbon-fluorine bond cleavage. II. Studies on the mechanism of the defluorination offluoroacetate. J. Bioi. Chem. 241 (1966) 5557-5559.
Goldman, P., et al.; Carbon-halogen bond cleavage. 3. Studies on bacterial halidohydrolases. J. Bioi. Chem. 243 (1968) 428-434.
Goldman, P.; The enzymatic cleavage of the carbon-fluorine bond in fluoroacetate. J. Bioi. Chem. 240 (1965) 3434-3438.
Goswami, A., et al., Inhibition by coumadin anticoagulants of enzymatic outer ring monodeiodination of iodothyronines Biochem. Biophys. Res. Commun. 104 (1982) 1231-1238.
Hayaishi, O. & Sutton, W.B. Enzymatic oxygen fixation into acetate concomitant with the enzymatic decarboxylation of L-lactate. J. Am. Chem. Soc. 79 (1957) 4809-4810.
Heppel, L.A. & Porterfield, V. T. Enzymatic dehalogenation of certain brominated and chlorinated compounds. J. Bioi. Chem. 176 (1948) 763-769.
Hollmann et al. "The First Synthetic Application of a Monooxygenase Employing Indirect Electrochemical NADH Regeneration," Chem Int. 2001. vol. 40 No. 1. pp. 169-171.
Hosokawa, K. & Stainer, R.Y. Crystallization and properties of p-hydroxybenzoate hydroxylase from Pseudomonas putida. J. Bioi. Chem. 241 (1966) 2453-2460.
International Preliminary Examination Report; Mar. 4, 2005, for PCT/US02/17407, 4 pages.
International Search Report & Written Opinion mailed Jul. 14, 2009, for PCT/US2009/040121, 6 pages.
International Search Report and Written Opinion mailed Feb. 20, 2012, for PCT/US12/49384, 9 pages.
International Search Report and Written Opinion mailed Jun. 14, 2012, for PCT/US11/61956, 8 pages.
International Search Report and Written Opinion mailed Mar. 29, 2013, for PCT/US12/58331 9 pages.
International Search Report; mailed Sep. 24, 2003, for PCT/US02/17407, 2 pages.
Jenkins, D.M. et al. Adaptation of a manometric biosensor to measure glucose and lactose, Biosensors Bioelectronics, Jan. 31, 2003, pp. 101-107.
Johannes, T.W. et al. (2005). Directed evolution of a thermostable phosphite dehydrogenase for NAD(P)H regeneration. Applied and Environmental Microbiology, 71 (10), 5728-5734. doi:10.1128/AEM. 71.10.5728-5734.2005.

(56) References Cited

OTHER PUBLICATIONS

Junker, F., et al; Dioxygenation and spontaneous deamination of 2-aminobenzene sulphonic acid in Alcaligenes sp. strain 0-1 with subsequent meta ring cleavage and spontaneous desulphonation to 2- hydroxymuconic acid. Biochem. J. 300 (1994) 429-436.
Keuning, S., Janssen, D. B. & Withol T, B.; Purification and characterization of hydrolytic haloalkane dehalogenase from Xanthobacter autotrophicus GJ10; J. Bacterial. 163 (1985) 635-639.
Kohler-Staub, D. & Leisinger, T.; Dichloromethane dehalogenase of Hyphomicrobium sp. Strain DM2. J. Bacterial. 162 (1985) 676-681.
Kumagai, H., et al; S-Carboxymethylecysteine synthase from *Escherichia coli*. Agric. Bioi. Chem. 53 (1989( 2481-2487.
Lee et al., "Proteome Changes after Metabolic Engineering to Enhance Aerobic Mineralization of cis-1, 2-Dichloreothylene," Journal of Proteome Research, 2006, pp. 1388-1397. American Chemical Society, Web.
Lipke, H. & Kearns, C. W.; W.; DDT dechlorinase. I. Isolation, chemical properties, and spectrophotometric assay. J. Bioi. Chem. 234 (1959) 2123-2128.
Lipke, H. & Kearns, C. W.; DDT dechlorinase. II. Substrate and cofactor specificity. J. Bioi. Chem. 234 (1959) 2129-2132.
Mars et al. "Effect of Trichloreothylene on Competitive Behavior of Toluene-Degrading Bacteria," Applied and Enviironmental Microbiology, 1998, vol. 64 (1), pp. 208-215.
McClay, K., B.G. Fox, and R.J. Steffan, "Chloroform Mineralization by Toluene-Oxidizing Bacteria," Applied and Environmental Microbiology, 1996. 62(8): pp. 2716-2722.
Mills, A. et al., Reversible, fluorescence-based optical sensor for hydrogen peroxide. Analyst 132 2007) 566-571.
Moorefield, H. H. Purification of DDT-dehydrochlorinase from resistant houseflies. Contr. Boyce Thompson Inst. 18 (1956) 303-310.
Moriguchi, M., et al.; Dehalogenation and deamination of 1-2-amino-4-choro-4-pentenoic acid by Proteus mirabillis. Agric. Bioi. Chem. 51 (1987) 3295.
Motosugi, M., et al.; Preparation and properties of 2-halo acid dehalogenase from Pseudomonas putida. Agric. Bioi. Chem. 46 (1982) 837-838.
Mulchandani A. et al; Biosensor for Direct Determination of Organophosphate Nerve Agents Using Recombinant *Escherichia coli* with Surface-Expressed Organophosphorus Hydrolase. 2. Fiber-Optic Microbial Biosensor. Analytical Chemistry 1998 70 (23), 5402-5046.
Muller, C. et al.; Multicomponent fiberoptica biosensor for use in hemodialysis monitoring; SPIE Biomedical Fiber Optic Instrumentation; vol. 2131; pp. 555-562 (Jul. 1994).
Muller, R., et al.; Incorporation of [180]water into 4-hydroxybenzoic acid in the reaction of 4-chlorobenzoate dehalogenase from Pseudomonas sp. CBS 3. Biochem. Biophys. Res. Commun. 124 (1984) 178-182.
Nagasawa, T., et al.; Physiological comparison of D-cysteine desulfhydrase of *Escherichia coli* with 3-chloro-D-alanine dehydrochlorinase of Pseudomonas putida CR 1-1. Arch. Microbial. 149 (1988) 413-416.
Nakagawa, H. and Takeda, Y. Phenol hydroxylase. Biochim. Biophys. Acta 62 (1962) 423-426.
Neujahr, Halina, "Determination of Phenol and Catechol Concentrations with Oxygen Probes Coated with Immobilized Enzymes of Immobilized Cells," Applied Biochemistry and Biotechnology, 1982, vol. 7, pp. 107-111.
Non-final Office Action issued in U.S. Appl. No. 12/100,308, mailed Apr. 6, 2015, 9 pages.
Nordlund, I. et al; "Complete nucleotides sequence and polypeptide analysis of multicomponent phenol hydroxylase from Pseudomonas sp. strain CF600," Journal of Bacterialology, 1990. 172: pp. 6826-6833.

Office Action issued in U.S. Appl. No. 14/348,426, mailed Apr. 2, 2015, 19 pages.
Pikus, J.D., et al; "Recombinant Toluene-4-Monoxygenase: Catalytic and Mossbauer Studies of the Purified Diiron and Rieski Components of a Four-Protein Complex," Biochemistry, 1996. 35: pp. 9106-9119.
Pilloton, R. et al., Lactose Determination in Raw Milk with a Two-Enzyme Based Electrochemical Sensor. Analytical Letters. 20 (1987) 1803-1814.
Plata, M.R. et al., State-of-the-art of (bio)chemical sensor developments in analytical Spanish groups', Sensors, Mar. 24, 2010, pp. 2511-2576.
Posch, H.E. & Wolfbeis. O.S., Optical sensor for hydrogen peroxide. Mikrochimica Acta 97 (1989) 41-50.
Rajendran, V., Lrudayaraj, J. Detection of glucose, galactose, and lactose in milk with a microdialysis-coupled flow injection amperometric sensor. J Dairy Sc. 85 (2002) 1357-1361.
Ramanathan, M. & Simonian, A.L.; Array biosensor based on enzyme kinetics monitoring by fluorescence spectroscopy: Application for neurotoxins detection; Biosensors and Bioelectronics 23 (2007) pp. 3001-3007.
Renganathan, V. Possible involvement of toluene-2-3-diocygenase in defluorination of 3-fluorosubstituted benzenes by toluene-degrading Pseudomonas sp. strain T-12. Appl. Exp. Microbial. 55 (1989) 330-334.
Rosenzwieg, A. C., et al. "Geometry of the Soluble Methane Monoxygenase Catalytic Diiron Center in Two Oxidation States," Chemistry and Biology, 1995. 2(6): pp. 409-418.
Rui et al. "Metabolic pathway engineering to enhance aerobic degradation of chlorinated ethenes and to reduce their toxicity by cloning a novel glutathione S-transferase, an evolved toluene o-monoxygenase, and y-glutamylcysteine synthetase," Environemental Microbiology, 2004, 6(5), pp. 491-500.
Schenk, T., et al.; Enzymatic dehalogenation of pentachlorophenol by extracts from Arthrobacter sp. strain ATCC 33790. J. Bacterial. 171 (1989) 5487-5491.
Scholtz, R., et al.; Characterization of 1-chlorohexane halidohydrolase, a dehalogenase of wide substrate range from an Arthrobacter sp. J. Bacterial. 169 (1987) 5016-5021.
Shaked, Z. & Whitesides, G.M., Enzyme-catalyzed organic synthesis: NADH regeneration by using formate dehydrogenase. J. Am. Chem. Soc. 102 (1980) 7104-7105.
Simonian, AL, et al.; FET-Based Biosensors for The Direct Detection of Organophosphate Neurotoxins; Electroanalysis 2004; 16, No. 22; pp. 1896-1906.
Smallridge, R. C., et al. "3', 5'-Diiodothyronine to 3'-Monoiodothyronine conversion in the fed and fasted rat: enzyme characteristics and evidence for two distinct 5'-deiodinases" Endocrinology 108 (1961) 2336-2345.
Stainthorpe, A. C., et al., "The Methane Monooxygenase Gene Cluster of Methylococcus capsulators (Bath)," Gene, 1990. 91: pp. 27-34.
Stokes et al. "An optical oxygen sensor and reaction vessel for high-pressure applications," Limnol. Ocearnogr., 1999, vol. 44(1):189-195.
Sundari, et al., "Retention of enzyme activity following freeze-drying the mycelium of ectomycorrhizal isolates: part II. Enzymes acting upon carbon compounds," World Journal of Microbiology and Biotechnology, vol. 16 (2000), pp. 865-868.
Suzuki, K., Takemori, S. and Katagiri, M. Mechanism of the salicylate hydroxylase reaction. IV. Flucrimetric analysis of the complex formation. Biochim. Biophys. Acta 191 (1969) 77-85.
Tkac J, et al., Novel glucose non-interference biosensor for lactose detection based on galactose oxidase-peroxidase with and without co-immobilised beta-galactosidase. Analyst. 125 (2000) 1285-1289.
Wichmann, R. & Vasic-Racki. D., Corfactor Regeneration at the Lab Scale. Adv Biochem Engine/Biotechnol 92 (2005) 225-260.
Woodyer, R.D. et al. Regeneration of cofactors for enzyme biocatalysis. Enzyme Technology, (2005) 85-103.

(56) References Cited

OTHER PUBLICATIONS

Yamada H., et al; Synthesis of D-cysteine from 3-chloro-D-alanine and hydrogen sulfide by 3-chloro-Dalanine hydrogen chloride-lyase (deaminating) of Pseudomonas putida. Biochem. Biophys. Res. Commun. 100 (1981) 1104-1110.

Yen, K.-M., "Construction of Cloning Cartridges for Development of Expression Vectors in Gram-Negative Bacteria," J. Bacterial., 1991. 173(17): pp. 5328-5335.

Yokota, T., et al.; Purification and properties of haloalkane dehalogenase from Corynebacterium sp. strain m15-3. J. Bacterial. 169 (1987) 4049-4054.

Zhao, H & van der Donk, W.A. Regeneration of cofactors for use in biocatalysis. Current Opinion in Biotechnology. 14 (2003) 583-589.

Zhong, Z. "Fiber Optic Enzymatic Biosensors and Biosensor Arrays for Measurement of Chlorinated Ethenes," Dissertation. Colorado State University, (submission date Apr. 2, 2011), 158 Pages.

Zhong, Z. et al., Fiber optic Monoxygenase biosensor for toluene concentration measurement in aqueous samples, Biosensors and Bioelectronics 26 (2011) 2407-2412.

Ziegler, D.M. and Pettit, F.H. Microsomal oxidases. I. the isolation and dialkylarylamine oxygenase activity of pork liver microsomes. Biochemistry 5 (1966) 2932-2938.

* cited by examiner

BIOSENSING SYSTEM WITH EXTENDED LIFETIME VIA COFACTOR RECYCLING

RELATED APPLICATIONS

This application is a national phase entry under 35 U.S.C. §371 of PCT/US2012/049384 filed Aug. 2, 2012, which claims priority under 35 U.S.C. §119(e) to U.S. Provisional Patent Application No. 61/514,309 filed Aug. 2, 2011, which is incorporated herein by reference in its entirety for all purposes. PCT/US2012/049384 claims priority to and is a continuation-in-part of U.S. patent application Ser. No. 13/562,592 filed on Jul. 31, 2012, application Ser. No. 13/562,592 is a continuation-in-part of U.S. patent application Ser. No. 12/100,308, filed Apr. 9, 2008, which claimed the benefit of priority to U.S. Provisional Patent Application Ser. Nos. 60/922,496, filed Apr. 9, 2007, and 61/024,453, filed Jan. 29, 2008, and which was a continuation-in-part of U.S. patent application Ser. No. 10/478,822, now U.S. Pat. No. 7,381,538, which was a national phase entry under 35 U.S.C. §371 of PCT/US02/17407, filed Jun. 1, 2002, which claimed the benefit of priority to U.S. Provisional Patent Application Ser. No. 60/295,211, filed Jun. 1, 2001.

GOVERNMENT RIGHTS

This invention was made with Government support under contract number BES-0529048 awarded by the National Science Foundation. The U.S. Government has certain rights in this invention.

BACKGROUND

Biosensors use biological components to detect an analyte of interest. Biosensors have the potential to be excellent alternatives or complements to traditional analytical chemical methods for environmental and process monitoring. A biosensor is capable of real-time analysis with simplicity of operation. Biosensors are often reagentless and can provide continuous, in-situ measurements as a cost effective alternative compared with traditional analytical methods.

SUMMARY

In one aspect, a biosensing system comprising a biocomponent is disclosed wherein the biocomponent comprises a whole cell containing oxygenase enzymes and dehydrogenase enzymes. In an embodiment, the nucleotide coding sequence of the oxygenase enzymes are on a plasmid within the whole cell biocomponent. In an embodiment, the nucleotide coding sequence of the dehydrogenase enzymes are encoded for on a plasmid within the whole cell.

In another aspect, a method for regenerating NADH and NADPH cofactors in a biosensing system is disclosed wherein a whole cell biocomponent comprises an oxygenase enzyme and a dehydrogenase enzyme. In one embodiment, an oxygenase enzyme is selected from the group consisting of monooxygenases and dioxygenases. In another embodiment, the oxygenase enzyme is toluene ortho-monooxygenase. In another embodiment, the oxygenase enzyme is a toluene ortho-monooxygenase variant. In another embodiment, the dehydrogenase enzyme is formate dehydrogenase.

In one aspect, a method for regenerating NADH and NADPH cofactors in a biosensing system is disclosed wherein a whole cell biocomponent comprises an oxygenase enzyme and a dehydrogenase enzyme and wherein a substrate for the dehydrogenase enzyme is delivered to the whole cell biocomponent. In one embodiment, the oxygenase enzyme is toluene ortho-monooxygenase. In one embodiment, the oxygenase enzyme is a toluene ortho-monooxygenase variant. In another embodiment, dehydrogenase enzyme is formate dehydrogenase and the substrate is formate. In one embodiment, the substrate is delivered through a capillary to the whole cell biocomponent. In another embodiment, the substrate is delivered through diffusion to the biocomponent.

In another aspect, a biosensing system that detects an analyte in a solution is disclosed. The system comprises a first biocomponent that catalyzes the reaction of the analyte and oxygen and uses a cofactor selected from the group consisting of NADH, NADPH, FADH, $FADH_2$, FMNH, and $FMNH_2$.

The system also comprises a second biocomponent that catalyzes the reaction of $NAD^+$, $NADP^+$, FAD, FADH, FMN, FMNH and an electron donor. The first biocomponent and the second biocomponent are within a whole cell biocomponent. The whole cell biocomponent is immobilized within a matrix and the matrix is in contact with a transducer layer. The transducer layer is part of an optode. In one embodiment, the whole cell biocomponent is alive. In another embodiment, the whole cell biocomponent is dead. In one embodiment, the transducer layer is a chemical transducer that interacts with oxygen. In another embodiment, the transducer layer is an optical transducer that interacts with oxygen. In one embodiment, the first biocomponent is selected from the group consisting of monooxygenases and dioxygenases. In another embodiment, the second biocomponent is formate dehydrogenase and the electron donor is formate. In one embodiment, the matrix comprises soluble formate. In one embodiment, the biosensing system has an optode comprising a distal tip of a capillary tube wherein the capillary tube contains formate or a salt of formate, and wherein the capillary tube is disposed to deliver the formate through the distal tip to the whole cell biocomponent.

In one aspect, a method for detecting the concentration of an analyte in a solution is disclosed wherein the analyte is a reactant in a reaction catalyzed by an oxygenase enzyme that requires a cofactor selected from the group consisting of NADH, NADPH, FADH, $FADH_2$, FMNH, and $FMNH_2$; and wherein a first biocomponent comprises an oxygenase enzyme; and wherein a second biocomponent comprises a dehydrogenase enzyme that catalyzes the reaction of an oxidized cofactor selected from the group consisting of $NAD^+$, $NADP^+$, FAD, FADH, FMN, and FMNH and an electron donor; and wherein a third biocomponent comprises an enzyme selected from the group consisting of epoxide hydrolase, glutathione synthetase, glutathione S-transferase and gamma-glutamylcysteine sythetase; and wherein the first biocomponent catalyzes the reaction of the analyte and the cofactor selected from the group consisting of NADH, NADPH, FADH, $FADH_2$, FMNH, and $FMNH_2$ while consuming oxygen and producing oxidized cofactor and an epoxide product; and wherein the oxidized cofactor is reduced by the second biocomponent; and wherein the epoxide product is a reactant in a reaction catalyzed by the third biocomponent; and wherein a transducer layer interacts with oxygen; and wherein the photons enter into a fiber optic cable and are transmitted to a photomultiplier; and wherein the photomultiplier produces an output signal that is input to an algorithm that transforms the signal generated by the photomultiplier into an output correlated to the concentration of the analyte in the solution. In one embodiment, the first biocomponent is toluene ortho-monooxygenase. In an embodiment, the first biocomponent is toluene ortho-monooxygenase. In an embodiment, the first biocomponent is a toluene ortho-monooxygenase variant. In one embodiment, the second biocomponent is formate dehydrogenase and the electron donor is formate. In one embodiment, the third biocomponent is selected from the group consisting of epoxide hydrolase, glutathione synthetase, glutathione S-transferase and gamma-glutamylcysteine sythetase.

In one aspect, a biosensing system for detecting the concentration of an analyte in a solution is disclosed wherein the analyte is a reactant in a reaction catalyzed by an oxygenase enzyme from Enzyme Commission numbers 1.13 and 1.14; and wherein the oxygenase enzyme requires a cofactor selected from the group consisting of NADH, NADPH, FADH, $FADH_2$, FMNH, and $FMNH_2$; and wherein a first biocomponent comprises an oxygenase enzyme; and wherein a second biocomponent comprises a dehydrogenase enzyme that catalyzes the reaction of an oxidized cofactor selected from the group consisting of $NAD^+$, $NADP^+$, FAD, FADH, FMN, and FMNH and an electron donor; and wherein a third biocomponent comprises an enzyme selected from the group consisting of epoxide hydrolase, glutathione synthetase, glutathione S-transferase and gamma-glutamylcysteine sythetase; and wherein the first biocomponent catalyzes the reaction of the analyte and the cofactor selected from the group consisting of NADH, NADPH, FADH, $FADH_2$, FMNH, and $FMNH_2$ while consuming oxygen and producing oxidized cofactor and an epoxide product; and wherein the oxidized cofactor is reduced by the second biocomponent; and wherein the epoxide product is a reactant in a reaction catalyzed by the third biocomponent; and wherein a transducer layer reacts interacts with oxygen; and wherein the photons enter into a fiber optic cable and are transmitted to a photomultiplier; and wherein the photomultiplier produces an output signal that is coupled to an algorithm that transforms the signal generated by the photomultiplier into an output correlated to the concentration of the analyte in the solution. In an embodiment, the first biocomponent is toluene ortho-monooxygenase. In an embodiment, the first biocomponent is toluene ortho-monooxygenase. In an embodiment, the first biocomponent is a toluene ortho-monooxygenase variant. In an embodiment, the second biocomponent is formate dehydrogenase and the electron donor is formate. In an embodiment, the first biocomponent, the second biocomponent and the third biocomponent all reside within a whole cell biocomponent that is immobilized within a matrix, and the matrix is adhered to the transducer layer.

In one aspect, a biosensing system for detecting the concentration of an analyte in a solution is disclosed wherein the analyte is a reactant in a reaction catalyzed by an oxygenase enzyme from Enzyme Commission numbers 1.13 and 1.14; and wherein the oxygenase enzyme requires a cofactor selected from the group consisting of NADH, NADPH, FADH, $FADH_2$, FMNH, and $FMNH_2$; and wherein a first biocomponent comprises an oxygenase enzyme; and wherein a second biocomponent comprises a dehydrogenase enzyme that catalyzes the reaction of an oxidized cofactor selected from the group consisting of NADH, NADPH, FADH, $FADH_2$, FMNH, and $FMNH_2$, and an electron donor; and wherein a third biocomponent comprises an enzyme selected from the group consisting of epoxide hydrolase, glutathione synthetase, glutathione S-transferase and gamma-glutamylcysteine sythetase; and wherein the first biocomponent catalyzes the reaction of the analyte and the cofactor selected from the group consisting of NADH, NADPH, FADH, $FADH_2$, FMNH, and $FMNH_2$ while consuming oxygen and producing oxidized cofactor and an epoxide product; and wherein the oxidized cofactor is reduced by the second biocomponent; and wherein the epoxide product is a reactant in a reaction catalyzed by the third biocomponent; and wherein a transducer layer reacts interacts with oxygen; and wherein the photons enter into a fiber optic cable and are transmitted to a photomultiplier; and wherein the photomultiplier produces an output signal that is coupled to an algorithm that transforms the signal generated by the photomultiplier into an output correlated to the concentration of the analyte in the solution. In an embodiment, the first biocomponent is toluene ortho-monooxygenase. In an embodiment, the first biocomponent is a toluene ortho-monooxygenase variant. In an embodiment, the second biocomponent is formate dehydrogenase and the electron donor is formate. In an embodiment, the first biocomponent, the second biocomponent and the third biocomponent all reside within a whole cell biocomponent that is immobilized within a matrix, and the matrix is adhered to the transducer layer.

In one aspect, a method for constructing biosensing systems having a linear response to the concentration of an analyte in a solution is disclosed wherein the biosensing system has an optode, and the optode has a fiber optical cable having a first tip and a second tip, and the first tip is covered by a transducer layer, and the transducer layer is covered by a biocomponent layer, and the biocomponent layer is covered by a porous layer, and the second tip is coupled to a photon-detection device, and the photon-detection device is coupled to a signal processing system, and the analyte concentration in the solution, the depth of the biocomponent layer, the depth of the porous layer, the diffusion coefficient of the porous layer, and the $K_m$ and $V_{max}$ of the reaction of the analyte that is catalyzed by the first biocomponent are selected such that the quotient between $Da^2$ and $4\beta$ is from about 10 to about 1000. In one embodiment, the first biocomponent is toluene ortho-monooxygenase. In one embodiment, the first biocomponent is a toluene ortho-monooxygenase variant. In one embodiment, the biocomponent has both a toluene ortho-monooxygenase variant and formate dehydrogenase. In another embodiment, the biocomponent has both a toluene ortho-monooxygenase variant and formate dehydrogenase, and also has at least one enzyme selected from an epoxide hydrolase, a glutathione synthetase, a glutathione S-transferase and a gamma-glutamylcysteine sythetase. In one embodiment, the transducer layer is RuDPP. In one embodiment, the porous layer is track-etched polycarbonate.

In one aspect, a biosensing system for detecting the concentration of an analyte in a solution is disclosed wherein the biosensing system has an optode, and the optode has a fiber optical cable having a first tip and a second tip, and the first tip is covered by a transducer layer, and the transducer layer is covered by a biocomponent layer, and the biocomponent layer is covered by a porous layer, and the second tip is coupled to a photon-detection device, and the photon-detection device is coupled to a signal processing system, and the analyte concentration in the solution, the depth of the biocomponent layer, the depth of the porous layer, the diffusion coefficient of the porous layer, and the $K_m$ and $V_{max}$ of the reaction of the analyte that is catalyzed by the first biocomponent are selected such that the quotient between $Da^2$ and $4\beta$ is from about 10 to about 1000. In one embodiment, the biocomponent is toluene ortho-monooxygenase. In one embodiment, the biocomponent is a toluene ortho-monooxygenase variant. In one embodiment, the biocomponent has both a toluene ortho-monooxygenase variant and formate dehydrogenase. In another embodiment, the biocomponent has both a toluene ortho-monooxygenase variant and formate dehydrogenase, and also has at least one enzyme selected from an epoxide hydrolase, a glutathione synthetase, a glutathione S-transferase and a gamma-glutamylcysteine sythetase. In one embodiment, the transducer layer is RuDPP. In one embodiment, the porous layer is track-etched polycarbonate.

In one aspect, a method for detecting the concentration of an analyte in a solution is disclosed wherein the analyte is a reactant in a reaction catalyzed by an oxygenase enzyme that requires a cofactor selected from the group consisting of NADH, NADPH, FADH, $FADH_2$, FMNH, and $FMNH_2$; and wherein a first biocomponent comprises an oxygenase enzyme; and wherein a second biocomponent comprises a dehydrogenase enzyme that catalyzes the reaction of an oxidized cofactor selected from the group consisting of $NAD^+$, $NADP^+$, FAD, FADH, FMN, and FMNH and an electron donor; and wherein the first biocomponent catalyzes the reaction of the analyte and the cofactor selected from the group consisting of NADH, NADPH, FADH, $FADH_2$, FMNH, and $FMNH_2$ while consuming oxygen and producing oxidized cofactor; and wherein the oxidized cofactor is reduced by the second biocomponent; and wherein a transducer layer interacts with oxygen; and wherein the photons enter into a fiber optic cable and are transmitted to a photomultiplier; and wherein the photomultiplier produces an output signal that is input to an algorithm that transforms the signal generated by the photomultiplier into an output correlated to the concentration of the analyte in the solution. In one embodiment, the first biocomponent is toluene ortho-monooxygenase. In an embodiment, the first biocomponent is toluene ortho-monooxygenase. In an embodiment, the first biocomponent is a toluene ortho-monooxygenase variant. In one embodiment, the second biocomponent is formate dehydrogenase and the electron donor is formate.

In one aspect, a biosensing system for detecting the concentration of an analyte in a solution is disclosed wherein the analyte is a reactant in a reaction catalyzed by an oxygenase enzyme from Enzyme Commission numbers 1.13 and 1.14; and wherein the oxygenase enzyme requires a cofactor selected from the group consisting of NADH, NADPH, FADH, $FADH_2$, FMNH, and $FMNH_2$; and wherein a first biocomponent comprises an oxygenase enzyme; and wherein a second biocomponent comprises a dehydrogenase enzyme that catalyzes the reaction of an oxidized cofactor selected from the group consisting of $NAD^+$, $NADP^+$, FAD, FADH, FMN, and FMNH and an electron donor; and wherein the first biocomponent catalyzes the reaction of the analyte and the cofactor selected from the group consisting of NADH, NADPH, FADH, $FADH_2$, FMNH, and $FMNH_2$ while consuming oxygen and producing oxidized cofactor and an epoxide product; and wherein the oxidized cofactor is reduced by the second biocomponent; and wherein a transducer layer reacts interacts with oxygen; and wherein the photons enter into a fiber optic cable and are transmitted to a photomultiplier; and wherein the photomultiplier produces an output signal that is coupled to an algorithm that transforms the signal generated by the photomultiplier into an output correlated to the concentration of the analyte in the solution. In an embodiment, the first biocomponent is toluene ortho-monooxygenase. In an embodiment, the first biocomponent is toluene ortho-monooxygenase variant. In an embodiment, the second biocomponent is formate dehydrogenase and the electron donor is formate. In an embodiment, the first biocomponent, and the second biocomponent all reside within a whole cell biocomponent that is immobilized within a matrix, and the matrix is adhered to the transducer layer.

In one aspect, a biosensing system for detecting the concentration of an analyte in a solution is disclosed wherein the analyte is a reactant in a reaction catalyzed by an oxygenase enzyme from Enzyme Commission numbers 1.13 and 1.14; and wherein the oxygenase enzyme requires a cofactor selected from the group consisting of NADH, NADPH, FADH, $FADH_2$, FMNH, and $FMNH_2$; and wherein a first biocomponent comprises an oxygenase enzyme; and wherein a second biocomponent comprises a dehydrogenase enzyme that catalyzes the reaction of an oxidized cofactor selected from the group consisting of NADH, NADPH, FADH, $FADH_2$, FMNH, and $FMNH_2$, and an electron donor; and wherein the first biocomponent catalyzes the reaction of the analyte and the cofactor selected from the group consisting of NADH, NADPH, FADH, $FADH_2$, FMNH, and $FMNH_2$ while consuming oxygen and producing oxidized cofactor and an epoxide product; and wherein the oxidized cofactor is reduced by the second biocomponent; and wherein a transducer layer reacts interacts with oxygen; and wherein the photons enter into a fiber optic cable and are transmitted to a photomultiplier; and wherein the photomultiplier produces an output signal that is coupled to an algorithm that transforms the signal generated by the photomultiplier into an output correlated to the concentration of the analyte in the solution. In an embodiment, the first biocomponent is toluene ortho-monooxygenase. In an embodiment, the first biocomponent is a toluene ortho-monooxygenase variant. In an embodiment, the second biocomponent is formate dehydrogenase and the electron donor is formate. In an embodiment, the first biocomponent, the second biocomponent and the third biocomponent all reside within a whole cell biocomponent that is immobilized within a matrix, and the matrix is adhered to the transducer layer.

DETAILED DESCRIPTION

Figure 1:
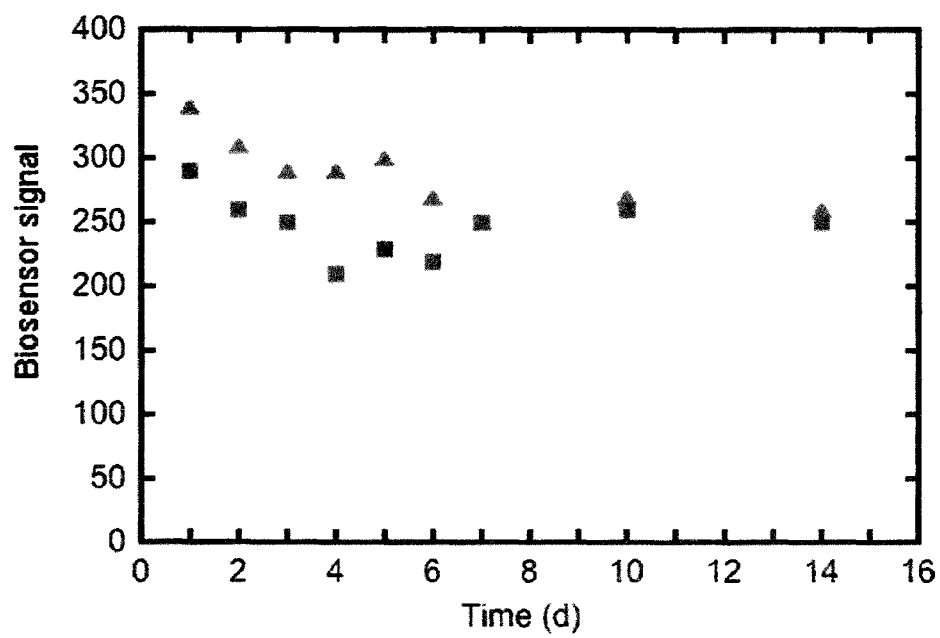
FIG. 1. Results of repeated measurements using two different toluene biosensing systems, both containing TOM and FDH.

Biosensing systems offer the potential of measurements of analytes or other molecules that are specific, continuous, rapid, and reagentless. Biosensing systems combine a biocomponent which is coupled to a transducer to yield a device capable of measuring chemical concentrations in a solution. A biocomponent may be any biological detection agent. Examples of biocomponents include enzymes, whole cells, microorganisms, RNA, DNA, viruses and antibodies.

Disclosed herein is a method of regenerating oxidation-reduction (redox) cofactors in enzymatic biosensing systems. Enzymatic biosensing systems that require cofactors usually stop working when the cofactor is depleted. The cofactor is often the reduced form of nicotine adenine dinucleotide (NADH), the reduced form of phosphorylated NADH (NADPH), and/or the reduced form of flavin adenine nucleotide ($FADH_2$, FAD), and/or the reduced form of flavin mononucleotide ($FMNH_2$, FMNH); after these reduced cofactors participate in an enzyme-catalyzed reaction, they are converted to a less energetic form, NAD+, NADP+, FADH, FAD, FMNH, FMN, respectively.

In living cells, the higher energy form of the cofactor (e.g., NAD(P)H) is regenerated as part of metabolism. Biosensing systems that have biocomponents that require these cofactors can work longer if there is a way to regenerate the higher energy form of the cofactor.

In one embodiment, biosensing systems have one biocomponent that catalyzes the reaction of an analyte of interest and a second biocomponent that regenerates NAD (P)H. The recycling of NAD(P)H with the second biocomponent requires the addition of an electron-donating molecule. The enzymes responsible for this recycling reaction are generally dehydrogenases of the Enzyme Commission number (EC number) EC 1, oxidoreductases, such as formate dehydrogenases (FDH), EC 1.2.1, for example.

Biosensing systems that use oxygenase enzymes as biocomponents typically require energy input in the form of a NAD(P)H cofactor. In one embodiment, oxygenases are monooxygenases EC 1.13 and/or dioxygenases EC 1.14. Genes for the enzymes toluene ortho-monooxygenase (TOM) and/or toluene ortho-monooxygenase-green (TOM-Green, a toluene ortho-monooxygenase variant) and formate dehydrogenase (FDH) may be cloned into plasmids and then introduced into *Escherichia coli* (*E. coli*) or may also be cloned directly into the chromosomal DNA of *E. coli*. TOM, TOM-Green and FDH may also be used as biocomponents exclusive of microorganisms and/or whole cells. The *E. coli* containing plasmids with genes encoding TOM and FDH may be used as biocomponents in a system that uses oxygenases while recycling cofactor NAD(P)H through FDH. These genes may also be encoded naturally on plasmid or chromosomal DNA in certain microorganisms that are useful as biocomponents.

The cofactors used in the biosensing systems may be pegylated by derivatizing with polyethylene oxide or otherwise modified to alter the diffusivity of the cofactor.

DEFINITIONS

Amperometric: Amperometric pertains to measurement of an electrical current.

Halogenated hydrocarbon: A halogenated hydrocarbon is a hydrocarbon chemical in which one or more halogen atoms are substituted for hydrogen atoms. The halogen atoms may be fluorine, chlorine, bromine, and/or iodine. Non-limiting examples of halogenated hydrocarbons include tetrachloroethene, trichloroethene, dichloroethene and monochloroethene and isomers thereof.

Toluene ortho-monooxygenase: Toluene ortho-monooxygenase (TOM) is an enzyme that belongs to the family of oxidoreductases. TOM oxidizes many substrates, including o-xylene, m-xylene, p-xylene, toluene, benzene, ethyl benzene, styrene, naphthalene, trichloroethene as well as tetrachloroethene. TOM uses oxygen and NADH as a cofactor to oxidize its substrate.

Toluene ortho-monooxygenase variant: Toluene ortho-monooxygenase (TOM) variants refer generally to any variant of TOM that has improved substrate binding kinetics, a faster turnover rate or other improved enzymological parameters over native TOM. One example of a TOM variant is TOM-Green which has a valine to alanine substitution (V106A) in the hydroxylase alpha-subunit of TOM from *Burkholderia cepacia* G4. NAD: NAD (nicotinamide adenine dinucleotide) used herein includes the oxidized form $NAD^+$ and the reduced form NADH. NAD is a cofactor.

NAD: NAD (nicotinamide adenine dinucleotide) used herein includes the oxidized form $NAD^+$ and the reduced form NADH. NAD is a cofactor.

NADP: NADP (nicotinamide adenine dinucleotide phosphate) used herein includes the oxidized form $NADP^+$ and the reduced form NADPH. NADP is a cofactor.

NAD(P)H: NAD(P)H is an inclusive term that embodies both the reduced form of nicotine adenine dinucleotide, NADH, and the reduced form of phosphorylated NADH, NADPH. NAD(P)H is a cofactor.

FAD: FAD (Flavin Adenine Dinucleotide) used herein includes FAD (fully oxidized form, or quinone form) that accepts two electrons and two protons to become $FADH_2$ (hydroquinone form). $FADH_2$ can then be oxidized to the semireduced form (semiquinone) FADH by donating one electron and one proton. The semiquinone is then oxidized once more by losing an electron and a proton and is returned to the initial quinone form, FAD. FAD is a cofactor.

FMN: FMN (Flavin Mononucleotide) used herein includes FMN (fully oxidized form), or FMNH (semiquinone form), and $FMNH_2$ (fully reduced form). FMN is a cofactor. In one embodiment, FMN is a prosthetic group for oxidoreductases.

Cofactor: A cofactor used herein is a non-protein chemical compound that is bound to a protein and is required for the protein's biological activity. Non-limiting examples of cofactors include: thiamine pyrophosphate, reduced and oxidized forms of flavin adenine mononucleotide (FAD), reduced and oxidized forms of flavin adenine mononucleotide (FMN), reduced and oxidized forms of nicotinamide adenine dinucleotide (NAD), reduced and oxidized forms of nicotinamide adenine dinucleotide phosphate (NADP), pyridoxal phosphate, lipoamide, methylcobalamin, cobalamine, biotin, coenzyme A, tetrahydrofolic acid, menaquinone, ascorbic acid, flavin adenine dinucleotide, coenzyme F420, adenosine triphosphate, S-adenosyl methionine, coenzyme B, coenzyme M, coenzyme Q, cytidine triphosphate, glutathione, heme, methanofuran, molybdopterin, nucleotide sugars, 3'-phosphoadenosine-5'-phosphosulfate, pyrroloquinoline, quinine, tetrahydrobiopterin, and tetrahydromethanopterin. Cofactors may also include metal ions such as $Ca^{2+}$, $Zn^{2+}$, $Fe^{2+}$, $Fe^{3+}$, $Mg^{2+}$, $Ni^{2+}$, $Cu^+$, $Cu^{2+}$, $Mn^{2+}$, and iron-sulfur clusters, for example.

Dehydrogenase: A dehydrogenase is an enzyme that oxidizes a substrate by transferring one or more hydrides ($H^-$) to an acceptor, usually $NAD^+/NADP^+$ or a flavin coenzyme such as FAD or FMN.

Measurement solution: A measurement solution is a solution in which an analyte may be dissolved to make a biosensor measurement. A non-limiting example of a measurement solution is 0.15 M NaCl and 0.025 M $CaCl_2$ at pH 7.0

Biocomponent: A biocomponent binds, catalyzes the reaction of or otherwise interacts with analytes, compounds, atoms or molecules thereby generating an atom, molecule or compound. Non-limiting examples of biocomponents include aptamers, DNA, RNA, proteins, enzymes, antibodies, cells, whole cells, tissues, single-celled microorganisms, and multicellular microorganisms. A biocomponent may be a cell, microorganism, cell organelle or any other membrane bound container that contains biocomponent enzymes within. A biocomponent may be purified or otherwise substantially isolated biocomponent enzymes. A biocomponent may be an unpurified extract of cells containing biocomponent enzymes.

Analyte: An analyte is the substance or chemical constituent that is desired to be detected or measured, such as the analyte concentration. With enzymatic biosensing systems, the analyte itself is not measured. Rather, a reaction of the analyte that is catalyzed by an enzymatic biocomponent causes a change in the concentration of a reactant or product that is measureable by the biosensing system. An analyte may also be a substrate of an enzyme.

Transducer: A transducer is a substance that interacts with the atoms, compounds, or molecules produced or used by the biocomponent. The interaction of the transducer with the atoms, compounds, or molecules produced or used by the biocomponent causes a signal to be generated by the transducer layer. The transducer layer may also generate a signal as an inherent property of the transducer. The signal may be an electrical current, a photon, a luminescence, or a switch in a physical configuration. In one embodiment, the signal produced by the transducer is quenched by a reactant or product of the biocomponent or may also be quenched by a molecule such as oxygen.

Chemical transducer: A chemical transducer is a chemical that catalyzes the reaction of an atom, molecule or compound and that reaction causes the production of a proton, oxygen molecule, luminescent event, photon or other atoms and molecules.

Optical transducer: An optical transducer is a material that luminesces. An optical transducer interacts with an atom, molecule, photon or compound and that interaction causes a change in the intensity and/or lifetime of the fluorescence of the optical transducer.

Physical transducer: A physical transducer is a material that interacts with an atom, molecule, photon or compound and that interaction causes a shift in its physical properties.

Biosensor: A biosensor measures the concentration of compounds, atoms or molecules using a biocomponent. A biosensor may also detect compounds, atoms or molecules using a biocomponent. A biosensor may also measure the toxicity of compounds, atoms or molecules using a biocomponent. A biosensor may alternatively be referred to as a biosensing system and/or a biosensing element.

Biosensing system: A biosensing system contains a biosensing element, a transducer, and a signal processing system. A biosensing system may alternatively be referred to as a biosensor system. Biosensing system may alternatively refer to various parts of the biosensing system such as the biosensing element, for example. A biosensing system may also contain a biosensing element, an optode, and a signal processing system.

Biosensing element: A biosensing element detects analytes. A biosensing element comprises one or more biocomponents and a transducer. In certain embodiments, a biosensing element comprises one or more biocomponents, a transducer and/or an optode.

Crosslinking: Crosslinking is the process of linking a biocomponent to a matrix. Crosslinking may be through chemical bonds, ionic interactions, physical entrapment or other modes and methods of linking a biocomponent to a matrix.

Matrix: A matrix is an interlacing, repeating cell, net-like or other structure that embodies the biocomponents. The immobilization material is an example of a matrix. A matrix may be a polymer.

Immobilization material: Immobilization material is the substance, compound or other material used to immobilize the biocomponent onto the biosensing element transducer layer. The immobilization material may be a matrix or may be less ordered than a matrix. The immobilization material may be a polymer such as cellulose acetate, polycarbonate, collage, acrylate copolymers, poly(ethylene glycol), polytetrafluroethylene (PTFE), agarose, alginate, polylysine, alginate-polylysine-alginate microcapsule, algal polysaccharides, agar, agarose, alginate, and carrageenan, polyacrylamide, polystyrene, polyurethane and other naturally occurring and synthetic polymers.

Polymer: Polymers as used herein include any natural or synthetic polymer including cellulose acetate, polycarbonate, collage, acrylate copolymers, poly(ethylene glycol), polytetrafluroethylene (PTFE), agarose, alginate, polylysine, alginate-polylysine-alginate microcapsule, algal polysaccharides, agar, agarose, alginate, and carrageenan, polyacrylamide, polystyrene, polyurethane and other naturally occurring and synthetic polymers. Polymers may be used to create a diffusivity barrier between the bulk solution and a biocomponent of a biosensing system. A polymer may be a porous layer.

Optode: An optode is a sensor device that measures the concentration of a specific substance usually with the aid of a transducer. An optode can be an optical sensor device that optically measures the concentration of a specific substance usually with the aid of a transducer. In one embodiment, for example, an optode requires a transducer, a polymer to immobilize the transducer and instrumentation such as optical fiber, a light source, detectors and other electronics. Optodes can apply various optical measurement schemes such as reflection, absorption, an evanescent wave, luminescence (for example fluorescence and phosphorescence), chemiluminescence, and surface plasmon resonance. Optodes may be fiber optical cable, planar wave guides or other surfaces conducive to the propagation of total internally reflecting light waves. An optode may be an optical transducer such as a photon detector.

pH sensor: A pH sensor measures the concentration of hydrogen ions in a solution.

pH optcode: A pH optode is an optode that has a detection element that interacts with hydrogen ions. An example of a detection element that interacts with hydrogen ions is fluorescein, fluoresceinamine or other fluorescein-containing compounds. In an embodiment, for example, a pH optode based on luminescence has a luminescent reagent that is pH responsive.

Luminescence: Luminescence is a general term which describes any process in which energy is emitted from a material at a different wavelength from that at which it is absorbed. Luminescence may be measured by intensity and/or by lifetime decay. Luminescence is an umbrella term covering fluorescence, phosphorescence, bioluminescence, chemoluminescence, electrochemiluminescence, crystalloluminescence, electroluminescence, cathodoluminescence, mechanoluminescence, triboluminescence, fractoluminescence, piezoluminescence, photoluminescence, radioluminescence, sonoluminescence, and thermoluminescence.

Fluorescence: Fluorescence is a luminescence phenomenon in which electron de-excitation occurs almost spontaneously, and in which emission from a luminescent substance ceases when the exciting source is removed. Fluorescence may be measured by intensity and/or by lifetime of the decay.

Phosphorescence: Phosphorescence is a luminescence phenomenon in which light is emitted by an atom or molecule that persists after the exciting source is removed. It is similar to fluorescence, but the species is excited to a metastable state from which a transition to the initial state is forbidden. Emission occurs when thermal energy raises the electron to a state from which it can de-excite. Phosphorescence may be measured by intensity and/or by lifetime of the decay.

Oxygen sensor: An oxygen sensor measures, or is responsive to, the concentration of oxygen in a solution.

Oxygen optode: An oxygen optode is an optode that has a transducer layer that interacts with oxygen. An example of a transducer layer that interacts with oxygen is tris(4,7-diphenyl-1,10-phenanthroline)Ru(II) chloride, also known as RuDPP.

Photon-detection device: A photon-detection device is a class of detectors that multiply the current produced by incident light by as much as 100 million times in multiple dynode stages, enabling, for example, individual photons to be detected when the incident flux of light is very low. Photon-detection devices may be vacuum tubes, solid state photomultipliers or other devices that interact with incident light, and amplify or otherwise process the signal and/or photons produced by that interaction. Alternative embodiments of a photon-detection device include an image sensor, CCD sensors, CMOS sensors, photomultiplier tubes, charge coupled devices, photodiodes and avalanche photodiodes.

Signal processing system: A signal processing system processes the signal from a biosensing system into information that can be displayed to an end user. An example of a signal processing system is a photon-detection device that detects the photons from the output of a photo optical cable of the optode of the biosensing system. The output of the photon-detection device is coupled to the input of a converter or sampler device such as a signal processor or a transimpedance amplifier. The output of the converter or sampler device is coupled to the input of a microprocessor that processes the output of the converter or sampler device into an output corresponding to the concentration of an analyte within the solution that was measured by the biosensing system. The output of the microprocessor is then communicated to an end user, for example by displaying the concentration on a screen.

Image sensor: An image sensor is a device that converts an optical image to an electric signal. Examples of image sensors include charge-coupled devices (CCD) or complementary metal-oxide-semiconductor (CMOS) active pixel sensors.

Sampler device: A sampler device reduces a continuous signal to a discrete signal. A common example is the conversion of a sound wave or light wave (a continuous signal) to a sequence of samples (a discrete-time signal).

Avalanche photodiode: An avalanche photodiode (APD) is a highly sensitive semiconductor electronic device that exploits the photoelectric effect to convert light to electricity. APDs can be thought of as photodetectors that provide a built-in first stage of gain through avalanche multiplication.

Converter: A converter is a current-to-voltage converter, and is alternatively referred to as a transimpedance amplifier. A converter is an electrical device that takes an electric current as an input signal and produces a corresponding voltage as an output signal. In another embodiment a converter may be a voltage-to-current converter.

Advantages

Advantages in using biosensing systems for measuring analytes include fast measurement, generally on the order of minutes. This is a big advantage over traditional methods like GC or HPLC in which a lot of time is spent in collection of the sample and extraction of analytes from the sample.

Small size is another advantage of using biosensing systems. Biosensing systems of the present disclosure have a compact design and are therefore capable of measurements in confined places such as needles and catheters in vivo and in conditions where weight is critical like spacecraft or airplanes.

Another advantage of using biosensing systems is that they can be used to measure the concentration of multiple analytes in a small sample in a continuous real-time measurement in a reversible manner with extremely low signal loss in an optical fiber as compared to electronic sensors such as amperometric assays. Furthermore, biosensing systems are capable of measuring at depths for applications such as groundwater monitoring.

An important advantage is the ability of biosensing systems to analyze complex samples with no prior preparation of samples. Biosensing systems can provide direct measurements in blood, food, and waste water, for example. This is important as removal of the sample from its environment (as in case of analyses by GC or HPLC) can change its chemistry and can thereby lead to inaccurate results. Also, this eliminates and simplifies sample separation steps and reduces the cost of the process. Measurements using biosensing systems can be made with minimum perturbations of the sample.

Biosensing systems have high specificity and sensitivity for measuring analytes of interest. Although most of the traditional methods (GC or HPLC) are very sensitive, they require expensive, laboratory-based hardware and trained operators. Other methods such as solid-phase enzyme-linked immunoassay (ELISA) may have good sensitivity but are generally not highly specific and cannot provide continuous measurements.

Another advantage for using biosensing systems of the present disclosure is the low cost of mass production compared to most of the traditional methods like GC or HPLC. Biosensing systems of the present disclosure are easy to use compared to traditional monitoring techniques such as gas chromatography, ion chromatography and high-pressure liquid chromatography. Biosensing systems using the proper biocomponents can also measure the toxicity of chemicals whereas analytical methods such as GC and HPLC can only measure concentration.

Biocomponents

Biocomponents react with, bind to or otherwise interact with an analyte. Reactive biocomponents produce or react with atoms, molecules or compounds that interact with the transducer.

Enzymes are proteins that can serve as biocomponents that catalyze reactions with their substrates. Substrates may be analytes. The products or reactants of the enzymatic reactions are usually measured by the biosensing system. In one embodiment, the products of the substrates that react with the analyte may themselves be acted upon and thereby produce additional products which may be measured by the biosensing system. Therefore, a biosensing system may measure primary, secondary or even higher orders of products caused by an initial reaction or binding of the analyte with the biocomponent.

Generally, enzymes for use in biosensing systems may be disposed within whole cells or extracted from cells and purified. Whole cells and microorganisms are also biocomponents. The cells and organisms used as biocomponents may or may not be living (able to replicate). Whether or not the cells are living, diffusion mechanisms and membrane-bound pumps may still be active that allow for the exchange of analytes and other compounds with the environment of the cell. It is often advantageous to use a dead cell or microorganism as a biocomponent at least because the proteolytic enzymes and pathways operating in a living cell may cease to function and the enzymes, for example, that are responsible for binding or reacting with the analytes therefore last longer than they would in a living cell. Another advantage of using dead cells or microorganisms is that if the biosensing system is used in-situ, such as in-line testing of milk being produced at a factory, there can be no contamination of the sample with cells or microorganisms that may infect or adulterate the sample.

Purified enzymes may be used as a biocomponent in biosensing systems. One benefit of using purified enzymes is that side reactions occurring within cells that result in the loss of enzyme activity may be avoided.

Enzymes isolated from extremophilic organisms such as hyperthermophiles, halophiles, and acidophiles may be used as biocomponents. They are often more resistant to losing their catalytic activity when compared to mesophilic enzymes.

An enzyme's resistance to becoming inactivated due to environmental factors, or even by the nature of the reaction that they catalyze, may be increased through mutagenic techniques. Such techniques are well known in the art and include various incarnations of changing the coding nucleotide sequence for the protein through various techniques. The proteins produced by expressing the mutagenic nucleotide sequences may then be tested for resistance to environmental factors and/or increased reactivity with substrates. Such an increase in reactivity may be due to advantageous binding specificity and/or increased kinetics of the binding and/or reaction catalyzed by the enzyme.

Methods of choosing cells and microorganisms that increase the response of the biosensing system may also be used to create biosensing systems that possess increased sensitivity, have quicker response times and last longer. Such techniques include directed evolution and using micro-assays to determine an increase in the production amount and/or rate of production of the molecules and/or atoms that react with the transducer layer.

Transducers

A transducer is a device that produces a measurable signal, or change in signal, upon a change in its chemical or physical environment. Transducers suited for biosensing systems that use enzymes as the biocomponent are those that interact with the reactants and/or products of the biocomponent and send a signal that is processed into a measurement reading. The nature of the interaction of the biological element with the analyte has a major impact on the choice of transduction technology. The intended use of the biosensing system imposes constraints on the choice of suitable transduction technique.

Amperometric transducers work by maintaining a constant potential on the working electrode with respect to a reference electrode, and the current generated by the oxidation or reduction of an electroactive species at the surface of the working electrode is measured. This transduction method has the advantage of having a linear response with a relatively simple and flexible design. Also, the reference electrode need not be drift-free to have a stable response. Since the signal generated is highly dependent on the mass transfer of the electroactive species to the electrode surface there can be a loss in sensitivity due to fouling by species that adsorb to the electrode surface. As a result of fouling, use of amperometric transducers is restricted where continuous monitoring is required. Enzymes, particularly oxidoreductases, are well suited to amperometric transduction as their catalytic activity is concerned with electron transfer.

Electroactive species that can be monitored at the electrode surface include substrates of a biological reaction (e.g., $O_2$, NADH), final products (e.g., hydrogen peroxide for oxidase reactions, benzoquinone for phenol oxidation) and also electrochemical mediators that can directly transfer electrons from the enzyme to the working electrode surface (e.g. hexacyanoferrate, ferrocene, methylene blue).

Potentiometric transducers work by having a potential difference between an active and a reference electrode that is measured under the zero current flow condition. The three most commonly used potentiometric devices are ion-selective electrodes (ISEs), gas-sensing electrodes and field-effect transistors (FETs). All these devices obey a logarithmic relationship between the potential difference and the activity of the ion of interest. This makes the sensors have a wide dynamic range. One disadvantage of this transducer is the requirement of an extremely stable reference electrode. Ion selective electrodes are commonly used in areas such as water monitoring. FETs are commercially attractive as they can be used to make miniaturized sensors, but manufacturing cost of FETs are high. Examples of potentiometric sensors are for acetaldehyde and cephalosporins, where the sensing electrode measures pH. Other examples are sensors used to measure creatinine, glutamine and nitrate with the sensing electrode detecting $NH_3$ gas.

Conductimetric transducers are often used to measure the salinity of marine environments. Conductance is measured by the application of an alternating current between two noble metal electrodes immersed in the solution. Due to specific enzyme reactions, they convert neutral substrates into charged products, causing a change in the conductance of the medium. This method can be used to make more selective and informative sensors by using multi-frequency techniques.

Optical transducers use optical phenomena to report the interaction of the biocomponent and the analyte. The main types of photometric behavior which have been exploited are ultraviolet and visible absorption, luminescence such as fluorescence and phosphorescence emission, bioluminescence, chemiluminescence, internal reflection spectroscopy using evanescent wave technology and laser light scattering methods.

One embodiment of an optical transducer uses luminescent reagents. In optical transducers that use luminescent reagents, a luminescent substance is excited by incident light, and as a result it emits light of a longer wavelength. The intensity and/or lifetime decay of emitted light changes when an atom, molecule or compound binds or otherwise interacts with the luminescent substance. The atom, molecule or compound may be a reactant or product of the biocomponent. Thus, if a reactant or product of the biocomponent catalyzes the reaction of the luminescent transducer and affects the intensity and/or lifetime decay of the light emitted by the transducer layer, the change in the measurement of the intensity and/or lifetime decay can be measured as a response to a particular analyte. There are several luminescent reagents that may be useful as optical transducers. Examples include Tris(4,7-diphenyl-1,10-phenanthroline)Ru(II) chloride, also known as RuDPP, for oxygen sensors, trisodium 8-hydroxy-1,3,6-trisulphonate fluorescein, fluoresceinamine and other compounds containing fluorescein for pH sensors, fluoro (8-anilino-1-naphthalene sulphonate) for $Na^+$ ion sensor and acridinium- and quinidinium-based reagents for halides.

Chemiluminescent and bioluminescent sensors work on principles similar to fluorescent sensors. Chemiluminescence occurs by the oxidation of certain substances, usually with oxygen or hydrogen peroxide, to produce visible light. Bioluminescence is, for example, the mechanism by which light is produced by certain enzymes, such as luciferase.

Calorimetric transducers use the heat generated from biological reactions and correlate it with the reaction conditions. In order to measure such small amounts of heat liberated during the reaction, a very sensitive device is required. In the calorimetric technique a very sensitive, electrical resistance thermometer is used to detect temperature changes down to 0.001° C. This method is advantageous, as it is independent of the chemical properties of the sample. Calorimetric transduction has been used in a wide range of areas, including clinical chemistry, determination of enzyme activity, monitoring gel filtration, chromatography, process control and fermentation.

An acoustic transducer uses materials such as piezoelectrics as a sensor transducer due to their ability to generate and transmit acoustic waves in a frequency-dependent manner. The optimal resonant frequency for acoustic-wave transmission is highly dependent on the physical dimensions and properties of the piezoelectric crystal. Any change in the mass of the material at the surface of the crystal will cause quantifiable changes in the resonant frequency of the crystal. There are two types of mass-balance acoustic transducers: bulk wave and surface acoustic wave. Acoustic transduction is a relatively cheap technique but it has the disadvantage of having low sensitivity with non-specific binding. This technique is commonly used to measure the concentration of volatile gases and vapors. A piezoelectric immunobiosensor for measuring an analyte of interest in drinking water may use a piezoelectric crystal coated with polyclonal antibodies that bind to that analyte. When the analyte molecules come into contact with the antibodies, they bond with the antibodies causing a change in the crystal mass, which in turn leads to a shift in the oscillation frequency and produces a measurable signal that can be measured and correlated to the concentration of the analyte of interest within the sample.

Optical and Signal Processing Systems

In an embodiment, biosensing systems of the present disclosure have a biocomponent, a transducer, a photon-detection device, and a signal-processing system. A signal processing system processes the signal from a photon-detection device into information that can be displayed to an end user. An example of a signal processing system is a microprocessor that accepts an input signal from a photon-detection device that is coupled to a biosensing element. The signal processing system then uses a software program that encodes an algorithm. The algorithm used by the software transforms the data provided by the input signal and provides an output signal that correlates to a numerical display of the concentration of an analyte that the biosensing system detected.

In an embodiment of the present disclosure, a biosensing system comprises biocomponent attached to a fiber optic pH optode, lens focusing system, photomultiplier (PMT), analog/digital (A/D) converter and a microprocessor. The biosensing element may be coupled to a polymethylmethacrylate (PMMA) optical fiber optic. The length of this connecting optical fiber may vary from 1 mm to well over 1 km. In an embodiment, the other end of this cable is attached to a light emitting diode (LED). In another embodiment, the other end of this cable is attached to a metal casing containing a 5 W halogen lamp or other light source and a lens focusing system. The light source should be able to operate at high temperatures, having a very short warm-up time in order to reach a constant power output. In one embodiment, light from the halogen lamp is first passed through a bandpass filter such as a 480-nm bandpass filter, for example. The light is then collected, paralleled and focused to the tip of fiber optic cable using a lens focusing system. An embodiment of the lens focusing system comprises spheric, aspheric, and convex lenses, and a dichroic mirror. Light from the lamp that radiates in opposite directions to the lens system may be refocused by the spheric lens and paralleled by the aspheric lens.

When light, for example light at 480 nm, is incident on a sensing tip coated with PVA/fluoresceinamine dye, fluorescence occurs. In an embodiment, this light is then passed back through a 520 nm bandpass filter or other bandpass filter having a frequency of light that is either blue or red shifted in comparison to the incident light wavelength, paralleled by focusing lens and then directed by the dichroic mirror onto the window of a single channel photo-detection device. The change in intensity and/or lifetime decay properties of the light can be measured. The photon detection device processes this light and the output potentiometric signal is sent to a computer interface using a connector block where it was converted into a digital signal by a data acquisition card. The final output is observed on a computer using software such as LabView software or other algorithmic software that interprets the signals from the sensing tip and processes them into correlating concentration measurements of the atom, compound, molecule or analyte of interest.

Immobilization of the Biocomponent

In order to construct a biosensing system, the biocomponent of the biosensing element of the biosensing system needs to be bound to or otherwise in contact with the transducer. This can be achieved by immobilizing the biocomponent on to the transducer. The viability of a biosensing system depends on the processing and type of material used for immobilizing the biocomponent. The material used for immobilizing the biocomponent may be referred to as a matrix, matrix material or as an immobilizing material.

Biocomponents may be very sensitive to the immobilizing process as well as the material that is used for immobilization. The pH, ionic strength, and any other latent chemistries of the gel matrix should be compatible with the biocomponent. The reactants and products of the reaction carried by the biocomponent should not affect the material used for immobilization. The biocomponent should be effectively immobilized and there should not be any leakage of the biocomponent from the matrix during the active lifetime of the biosensing system. The immobilization material should be non-toxic and non-polluting. The material should have proper permeability to allow sufficient diffusion of substrates, products and gases. The matrix material should allow for sufficient cell activity and cell density. The immobilization material should protect the biocomponent from biotic and abiotic environmental stresses that would lower biocomponent activity or lifetime.

Techniques of Immobilization

In one embodiment, adsorption is used to immobilize the biocomponent. Many substances adsorb enzymes, cells, microorganisms and other biocomponents on their surfaces, e.g., alumina, charcoal, clay, cellulose, kaolin, silica gel and collagen. Adsorption can be classified as physical adsorption (physisorption) and chemical adsorption (chemisorption). Physisorption is usually weak and occurs via the formation of van der Waals bonds or hydrogen bonds between the substrate and the enzyme molecules. Chemisorption is much stronger and involves the formation of covalent bonds. Adsorption of the biocomponent may be specific through the interaction of some moiety, link or other reactive component of the biocomponent or may be non-specific.

In another embodiment, microencapsulation is used to immobilize the biocomponent. In this method, a thin microporous semipermeable membrane or layer is used to surround the biocomponent. In one embodiment whole cell biocomponents may be microencapsulated. In another embodiment, purified or otherwise substantially isolated enzyme biocomponents may be microencapsulated. Because of the proximity between the biocomponent and the transducer and the very small thickness of the membrane, the biosensing element response is fast and accurate, and there is always an option of bonding the biocomponent to the fiber optical portion of the biosensing system via molecules that conduct electrons, such as polypyrrole, for example. The membrane used for microencapsulation may also serve additional functions such as selective ion permeability, enhanced electrochemical conductivity, mediation of electron transfer processes, or controlling the sensitivity of the response of the biosensing system. Examples of membranes that may be used for microencapsulation immobilization of biocomponents are cellulose acetate, polycarbonate, collage, acrylate copolymers, poly(ethylene glycol) and polytetrafluroethylene (PTFE). Additional materials that may be used are agarose, and alginate and polylysine, which together form an alginate-polylysine-alginate microcapsule.

In another embodiment, entrapment is used to immobilize the biocomponent. In this method, cells are physically constrained (entrapped) to stay inside a three-dimensional matrix. The materials used for entrapment must allow uniform cell distribution, biocompatibility and good transport of substrates, cofactors and products. Both natural and synthetic materials (like alginate, agarose and collagen) may be used for entrapment.

In another embodiment, hydrogels are used to immobilize the biocomponent. Hydrogels provide a hydrophilic environment for the biocomponent and they require only mild conditions to polymerize. Hydrogels are capable of absorbing large quantities of water which can facilitate enzymatic biocomponent reactions such as hydrolysis. Both natural and synthetic hydrogels may be used such as algal polysaccharides, agar, agarose, alginate, and carrageenan, polyacrylamide, polystyrene and polyurethane.

Alginate, a hydrogel, provides a good, biocompatible microenvironment for the biocomponent and has a gentle encapsulation process. It is a naturally occurring linear polymer composed of β-(1,4) linked D-mannuronic acid and a-(1,4)-L-guluronic acid monomers. Commercially, alginate is obtained from kelp, but bacteria such as *Azotobacter vinelandii*, several *Pseudomonas* species and various algae also produce it. When alginate is exposed to $Ca^{2+}$ ions, a cross-linking network is formed by the bonding of $Ca^{2+}$ ions and polyguluronic portions of the polymer strand by a process known as ionic gelation. The gelation process is temperature-independent. Complete gelling time without biocomponents may be from about 1 minute to greater than about 30 minutes. Gelling time usually increases with an increase in biocomponent density and decreases with an increase in $CaCl_2$ concentration.

In another embodiment, sol-gels may be used to entrap biocomponents into silicate networks. Sol-gels may require milder polymerization processes and create matrices that exhibit good mass transport and molecular access properties particularly for electrochemical and optical transduction modes.

In another embodiment, cross-linking is used to immobilize the biocomponent. Cross-linking chemically bonds the biocomponent to solid supports or to other supporting materials such as a gel. Bifunctional agents such as glutaraldehyde, hexamethylene diisocyanate and 1,5-dinitro-2,4-difluorobenzene may be used to bind the biocomponent to the solid support such as a matrix, for example. Cross-linking produces long-term stability under more strenuous experimental conditions, such as exposure to flowing samples, stirring, washing, etc.

In another embodiment, covalent bonding is used to immobilize the biocomponent. Covalent bonding uses a particular group present in the biocomponent, which is not involved in catalytic action, and attaches it to the matrix, transducer layer, membrane, porous layer, or fiber optical surface through a covalent bond. The radicals that take part in this reaction are generally nucleophilic in nature (e.g., —$NH_2$, —COOH, —OH, —SH and imidazole groups).

Stabilization

Biosensing systems of the present disclosure are stable and long-lived, can stand prolonged storage and can also perform consistently when used for extended periods. Biocomponents may be stabilized through various means, depending upon the type of biocomponent and transducer used.

In one embodiment, the biocomponent may be stabilized through molecular modification. Molecular modification improves the stability of enzymes, and other biocomponents, through changing certain amino acids or nucleotides in the peptide or nucleic acid sequence, respectively. Molecular modifications may increase the temperature stability of various enzymes by modifying the amino acids at the catalytically active enzyme reaction site or at structurally sensitive amino acid sequences, through site-directed mutagenesis.

Another method for improving the stability of biocomponents, such as enzymes, is through glycosylation. Since glycosylated proteins are very stable, grafting or otherwise bonding polysaccharides or short chains of sugar molecules onto protein molecules usually improves the stability of the biocomponent.

In one embodiment, the biocomponent may be stabilized through cross-linking. Cross-linking of the biocomponent may occur through covalent bonding, entrapment, encapsulation and other immobilization techniques or processes. These immobilization processes can improve enzyme stability by reducing the biocomponent's mobility and thereby reducing degradation of its three-dimensional structure. In addition, cross-linking prevents the loss of biocomponents from the matrix in which they are immobilized. Using the entrapment method discussed above, the loss of biocomponents may further be reduced by the addition of certain gel-hardening agents such as glutaraldehyde, polyethyleneimine, hexamethylenediamine and formaldehyde.

In another embodiment for stabilizing the biocomponent, freeze drying, also known as lyophilization, may be used. Freeze drying is a method for long-term preservation of microorganisms and enzymes. It involves removal of water from frozen bacterial suspensions by sublimation under reduced pressure. The lyophillization is performed in the presence of cryoprotective agents such as glycerol and DMSO which reduce the damage caused during freezing and during thawing. Lyophillized biocomponents, for example dried cells, are stable to degradation by keeping the lyophilized biocomponents below 4° C., and away from oxygen, moisture and light. Even after prolonged periods of storage, such as about 10 years, lyophillized biocomponents may then be rehydrated and restored to an active state. Two examples of lyophilizing techniques used on biocomponents include centrifugal freeze-drying and prefreezing.

In another embodiment, the biocomponents by be stabilized through heat shocking. Heat shocking involves heating vacuum-dried cells at a high temperature (about 300° C., for example) for a very short time (about 2-3 minutes, for example). With the proper combination of temperature and heating time, biocomponents such as whole cells and microorganisms can be killed but still retain an active enzyme system that may be used to detect a compound of interest. These dead cells and microorganisms can be kept for a long time away from moisture without any requirement of nutrients.

In another embodiment, the addition of carbohydrates and other polymers will stabilize the biocomponents. Carbohydrates used to stabilize biocomponents include polyalcohols and various sugars such as trehalose, maltose, lactose, sucrose, glucose and galactose, for example. This stabilization may occur due to the interaction of polyhydroxyl moieties from the polyalcohols and/or sugars with water with the biocomponents, thus increasing hydrophobic interactions and keeping the biocomponents in a stable conformation.

In an additional embodiment, stabilization of the biocomponents may occur through freezing the biocomponents. When a biocomponent is frozen, the metabolic activities may be reduced considerably. Storage of the biosensing system, and/or biosensing element at temperatures at which the biocomponents remain frozen may increase the stability and life-time of the biosensing system.

Biosensing Elements

Several biosensing system designs are disclosed herein including biosensing elements on the tip of a fiber optical cable, and biosensing elements displaced upon a surface, for example. The biosensing system may be based on an optical pH or optical oxygen sensor. Oxygenases may be used alone as the biocomponent or in conjunction with other biocomponents. The biosensing elements may be separate from one another or combined into the same tip or biosensing element.

Some biosensing systems are made using food-grade enzymes and materials. These biosensing systems are advantageously used for measuring analytes in food products.

In an embodiment, the disclosures presented herein are a set of biosensing system designs based on optical transduction. Optical enzymatic biosensing system designs using an optical signal transaction are more robust and less susceptible to chemical interference than electrochemical (e.g., amperometric) methods. In one embodiment, optical pH and optical oxygen sensors (optodes) employ fluorophores that are sensitive to either protons ($H^+$ ions) or molecular oxygen. Optical enzymatic biosensing elements are formed by combining a transducer and/or optode with a biocomponent that catalyzes a reaction with the analyte and results in altered pH or oxygen.

Biosensing System Detection at High Analyte Concentrations

Some biosensing system applications may require the measurement of relatively high analyte concentrations. These concentrations are high enough to saturate the response of the biocomponent, meaning that all of the binding sites of an antibody or all of the enzymatic reaction sites are occupied. Under these saturating conditions, the biosensing system response is no longer dependent upon the analyte concentration and no measurement can be made.

One embodiment of the present disclosure is for optical enzymatic biosensing systems for the measurement of analytes at high concentrations. Optical enzymatic biosensing systems for the measurement of analytes at high concentrations and the concepts disclosed herein are broadly applicable for the measurement of many different kinds of analytes in solutions such as the measurement of halogenated hydrocarbons, for example.

Figure 3:
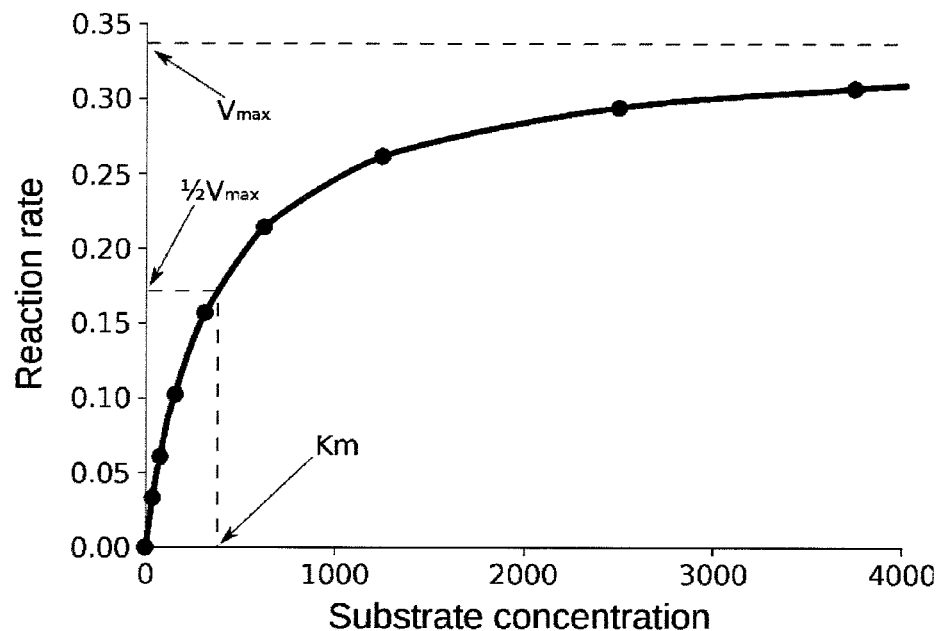
FIG. 3. Graphical representation of Michaelis-Menten equation relationships between enzyme reaction rate and substrate concentration.

Optical enzymatic biosensing systems may use biosensing elements that may be constructed as thin enzyme-containing films deposited or placed over an optical transducer layer. The response of these biosensing systems (signal as a function of analyte concentration) is governed by the rate of the enzymatic reaction and the manner in which that rate depends on the analyte concentration. For most enzymes, this relationship is the saturation type shown in FIG. 3 in which the rate depends nearly linearly on analyte concentration at low concentrations but becomes independent of concentration at high concentrations. For a biosensing system that has a biosensing element with a thin-layer biocomponent, this means that the biosensing system response becomes saturated and consequently it is not possible to distinguish one high concentration value from another.

To describe this high concentration range more accurately, it is convenient to use the Michaelis-Menten equation, which relates the enzymatic reaction rate $R_{enz}$ to the concentration of the analyte ($C_A$) as $R_{enz}=kC_E C_A/(K_M+C_A)$ in which k and $K_M$ are parameters of the enzymatic reaction rate (depending on the enzyme and the analyte) and $C_E$ is the concentration of enzyme. The combined term $kC_E$ is frequently presented as $V_{max}$, the maximum reaction rate ("velocity"). The Michaelis-Menten equation has been found to accurately describe many different enzyme-catalyzed reactions.

When analyte concentrations are low enough that $C_A$ is much less than $K_M$, the MichaelisMenten equation approximately reduces to a first-order (linear) dependence of the reaction rate on the analyte concentration, $R_{enz}=(V_{max}/K_M)C_A$. This linear response is the desired operating condition for a biosensing system. However, for thin-film enzymatic biocomponent biosensing systems, this range extends only to values of $C_A$ that are small relative to $K_M$; "small" can be interpreted as 10% or less. At higher analyte concentrations, the relationship of the enzymatic reaction rate to the analyte concentration, and thus the relationship of the biosensing system response to the analyte concentration, becomes increasingly nonlinear. Once the analyte concentration becomes much larger than $K_M$ such that $C_A+K_M \approx C_A$, the enzymatic reaction rate and the biosensing system response become essentially independent of $C_A$. Modifying the Michaelis-Menten equation for this case of $C_A \gg K_M$ yields $R_{enz}=V_{max}$ The analysis above is based on the assumption that the analyte concentration in the vicinity of the biocomponent enzyme molecules ("local" concentration) is the same as in the solution in which the biosensing element is placed ("bulk solution" concentration). However, this situation can be manipulated such that the local concentration is lowered such that it falls within the linear measurement range. The local concentration can be related to the bulk solution concentration by either calculating the reaction-diffusion behavior of the system or through experimental calibration procedures.

A solution to extend the linear (useful) measurement range of optical enzymatic biosensing systems beyond that available with thin-film designs is to add a mass transfer (diffusion) barrier. This diffusion barrier may take the form of a polymer coating, a membrane, a porous layer, or any other material through which the analyte passes more slowly than through the measurement medium. In an embodiment, the mass transfer barrier is a layer of a polymer coating whose thickness is varied to correspond to the linear measurement range of a biosensing system for a given bulk solution. An effective diffusion barrier could also be created by increasing the thickness of the enzyme layer. Biosensing systems that have an increased thickness of the enzyme layer are generally referred to as thick-film biosensing systems. Linear measurement ranges can be extended through the use of thick-film biosensing system designs. The rates of analyte mass transfer and reaction remain coupled in thick-film biosensing system designs. Thus, at some analyte concentration, the rate of mass transfer is high enough that the analyte concentration near the enzymes exceeds the linear reaction rate range and the biosensing system no longer has a direct, linear response to the analyte concentration.

In one embodiment, biosensing systems of the present disclosure use a design scheme for the construction of optical enzymatic biosensing systems capable of measurements at high analyte concentrations. This is based on the combination of a high mass transfer resistance and a high enzyme concentration, so that the analyte concentration near the transducer/fluorophore layer always remains in the linear reaction rate (and biosensing system response) range.

For any given concentration of any particular analyte, the appropriate ranges of the mass transfer coefficient of the analyte or substrate from the bulk solution to the enzyme layer, and the reaction rate parameters of the enzyme layer can be determined according to Equation 1: $(((Da+1-\beta)^2)/4\beta) \gg 1$. Where $\beta$=the substrate concentration in the bulk solution divided by the $K_M$ of the enzyme for the substrate; and where Da is $(h_e V_{max} h_p)/(D_p K_M)$ where $h_e$ is the thickness of the enzyme layer which is embedded within a matrix; $h_p$ is the thickness of a porous polymeric or ceramic material which sits atop the enzyme layer; where $D_p$ is the diffusion coefficient of the polymer coating, see FIG. 4.

Figure 4:
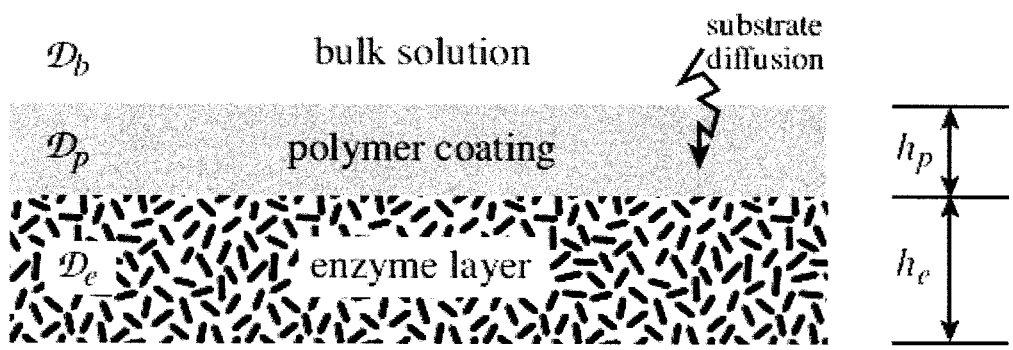
FIG. 4. Representation of optical enzymatic biosensing element portion of a biosensing system for measuring analytes in high concentrations.

Therefore, by using Equation 1, the calculations provide specific design parameters such as the thickness of the enzymatic (detection) and mass transfer resistance layers such that a linear biosensing system response is obtained for a given concentration, see FIG. 4.

As an example of different embodiments of biosensing systems of the present disclosure, a series of biosensing systems were constructed with different membranes/porous layers or no membrane/porous layer covering the enzyme layer. The analyte concentration that was measured was lactose, but this series of biosensing systems is representative for any analyte or substrate, such as halogenated hydrocarbons, for example. In one embodiment, biosensing system A, the biosensing system has only a thin film of enzyme that is immobilized on the surface of the biosensing system that is exposed to the solution. In another embodiment, biosensing system B, the biosensing system has a porous layer placed over the same thickness of enzyme layer as was used in biosensing system A. In another embodiment, biosensing system C, the same thickness of enzyme layer as biosensing systems A and B has a membrane layer/porous layer placed over it that is less porous than the porous layer of biosensing system B.

Biosensing systems B and C have a membrane material consisting of track-etched polycarbonate with a pore size of 0.015 μm. Additional mass transfer resistance was provided for biosensing system C by casting a polyurethane coating on top of the porous layer material.

Figure 5:
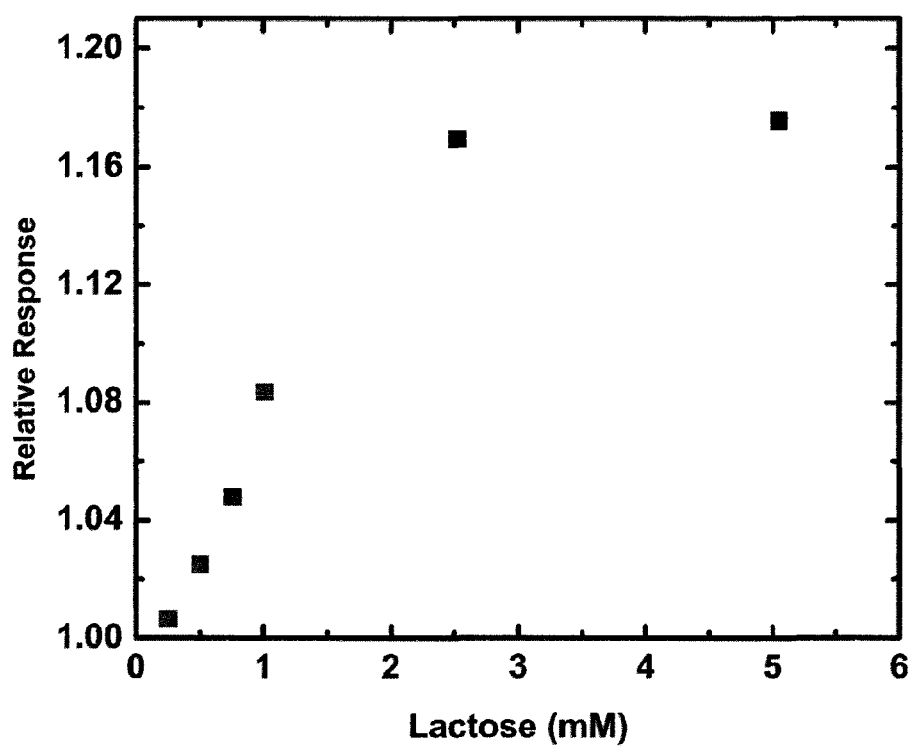
FIG. 5. Response curve for biosensing system A. Biosensing system A is a lactose biosensing system with a thin film of enzyme immobilized on the surface.

The response of biosensing system A to a series of lactose standards is shown in FIG. 5. From FIG. 5 it is seen that the biosensing system response begins to saturate at concentrations above 1.01 mM lactose. Signal saturation is due to the presence of analyte at concentrations that exceed the $K_M$ of the enzyme.

Figure 6:
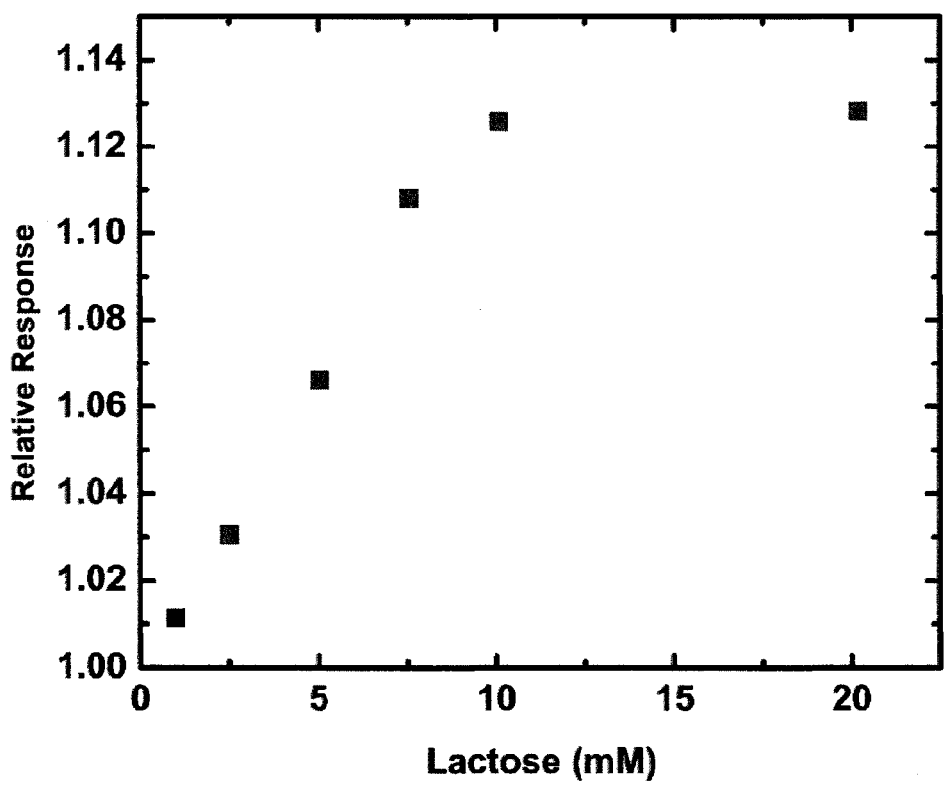
FIG. 6. Response curve for biosensing system B. Biosenor system B is a lactose biosensing system with a porous diffusive barrier.

Biosensing system B has the addition of a diffusive barrier on top of the enzyme layer. This diffusive barrier extended the linear range of biosensing system B into higher concentration ranges, see FIG. 6. For biosensing system B, a porous polycarbonate membrane was immobilized on top of the enzyme layer to act as barrier to analyte mass transfer, which resulted in a lower analyte concentration in the enzyme layer compared to that in bulk solution.

Figure 7:
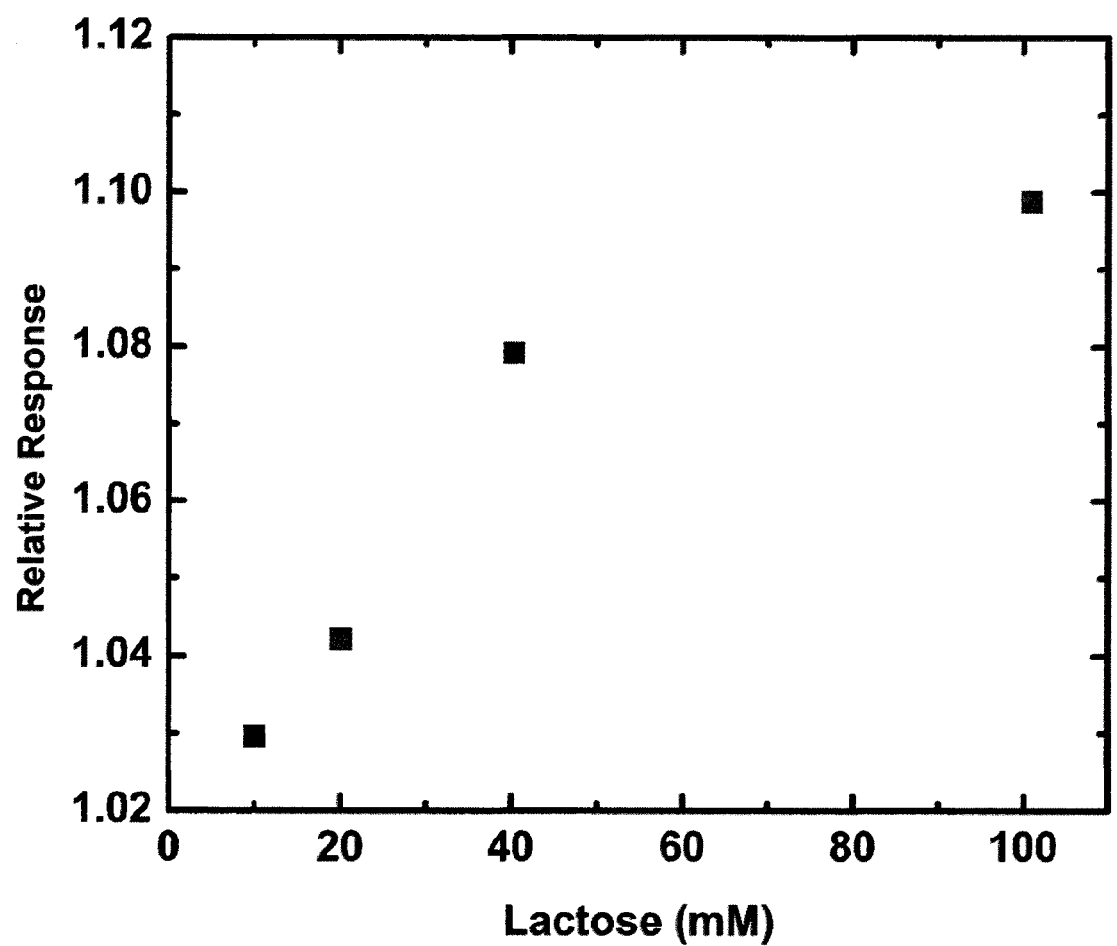
FIG. 7. Response curve for biosensing system C. Biosensing system C is a lactose biosensing system having a less porous diffusive barrier compared to the porous diffusive barrier used in biosensing system B.

Biosensing system C used a less porous polycarbonate membrane relative to the membrane of biosensing system B. This decrease in the porosity of the diffusive barrier resulted in the ability to measure lactose at even higher concentrations relative to biosensing system B, see FIG. 7. The linear range of biosensing system C was extended into this higher concentration regime as a direct result of the increased mass transfer resistance of the less porous diffusive barrier.

Figure 8:
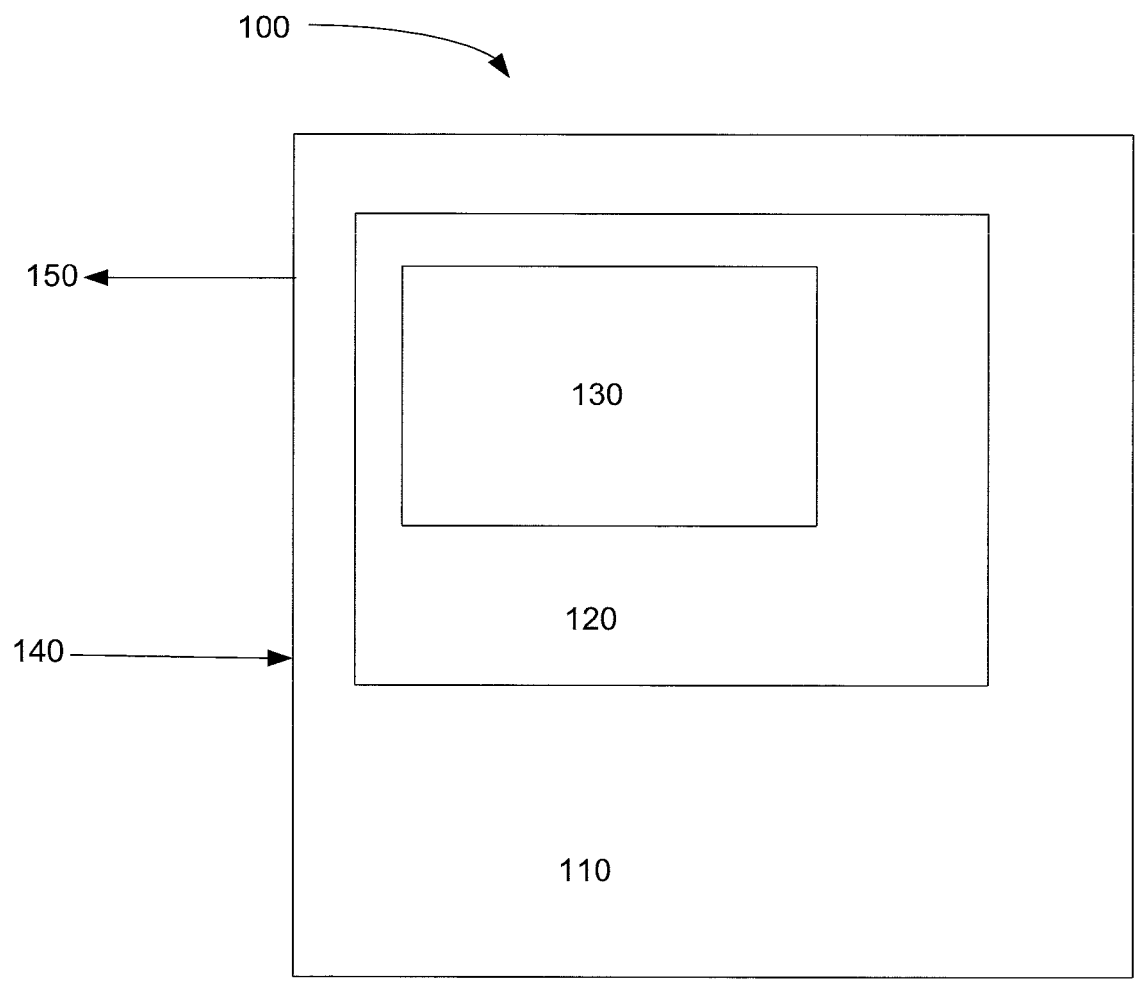
FIG. 8. System for providing design parameters used for constructing biosensing elements.

FIG. 8 shows one exemplary embodiment of a system 100 that is used to provide the appropriate design parameters for constructing biosensing elements used in biosensing systems that have a linear response in a given range of an analyte concentration in a solution. System 100 uses a computer 110 that has a microprocessor 120 that contains software 130 that processes input data 140 to provide output data 150 that contains the appropriate design parameters used for constructing biosensing elements used in biosensing systems that have a linear response in a given range of an analyte concentration in a solution. Output data 150 is displayed upon a screen or saved in a memory storage device or may be transmitted to another memory device or display device.

Constructing the Biosensing System and/or Biosensing Element

In an embodiment, the biosensing element is constructed by putting an immobilized biocomponent within a matrix and coupling that biocomponent-containing matrix onto a transducer. In another embodiment, a biosensing system is created by bonding, affixing or otherwise causing the biocomponent to be in contact with an optode.

Figure 9:
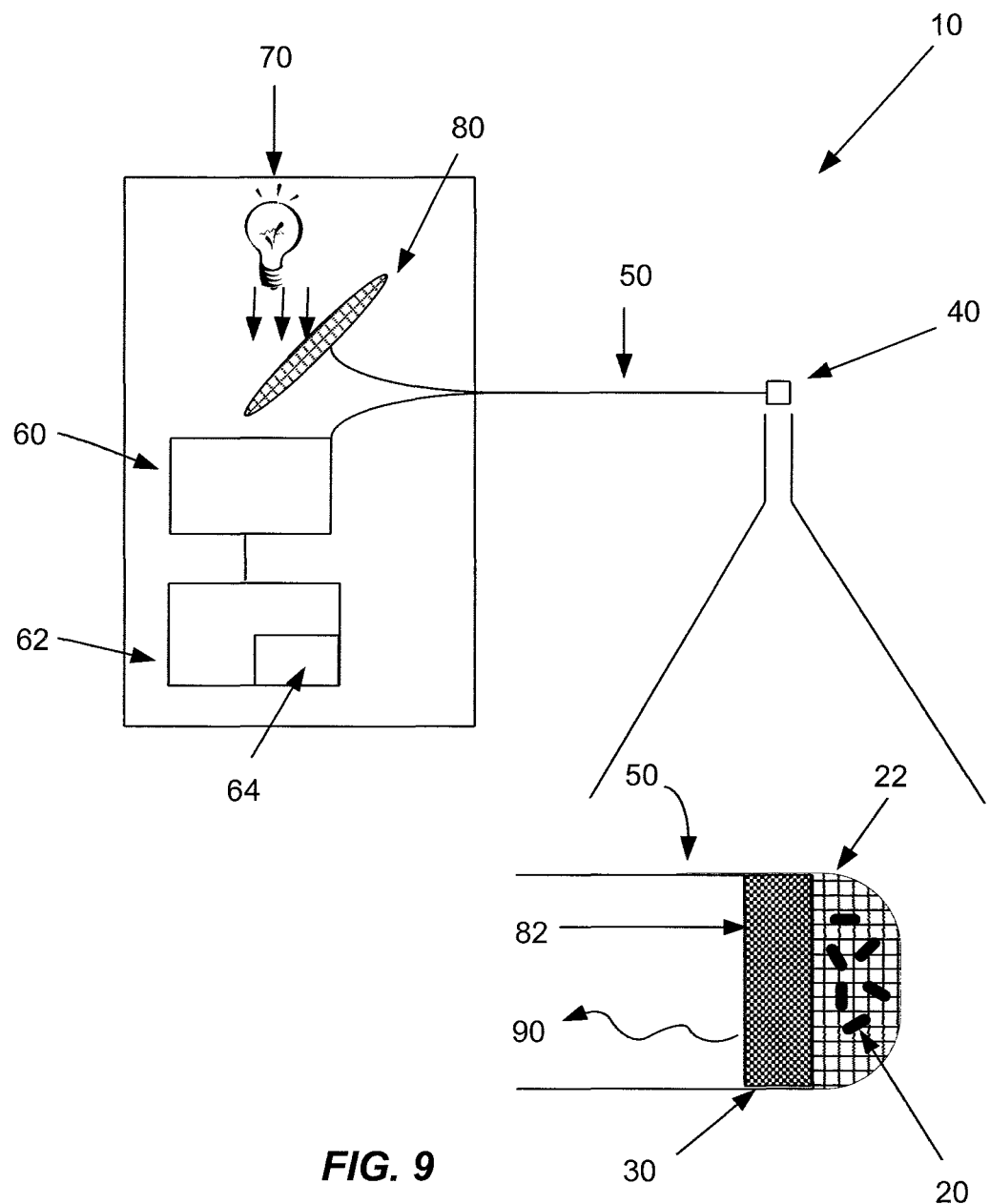
FIG. 9. Schematic representation of a biosensing system.

An embodiment of biosensing system of the present disclosure is depicted in FIG. 9. FIG. 9 depicts a biosensing system 10. Biosensing system 10 includes a biocomponent 20 that is displaced within a matrix 22. Matrix 22 is in direct contact with a transducer 30. Transducer 30 is in direct contact with an end of a bifurcated optical cable 50. Biocomponent 20 and transducer 30 comprise a biosensing element 40. Bifurcated optical cable 50 transmits light from a light source 70 through a filter 80. The light that is transmitted through filter 80 is transmitted through bifurcated optical cable 50 at a first light wavelength 82. Transducer 30 interacts with first light wavelength 82 and luminesces at a second light wavelength 90. Second light wavelength 90 is transmitted through bifurcated optical cable 50 and is detected by a photon-detection device 60 that produces a signal that is sent to a signal processing system 62. Signal processing system 62 contains software 64 that uses an algorithm for determining the concentration of an analyte in a solution based on the luminescence of transducer 30 at second wavelength 90.

Method of Using the Biosensing System and/or Biosensing Element

Figure 10:
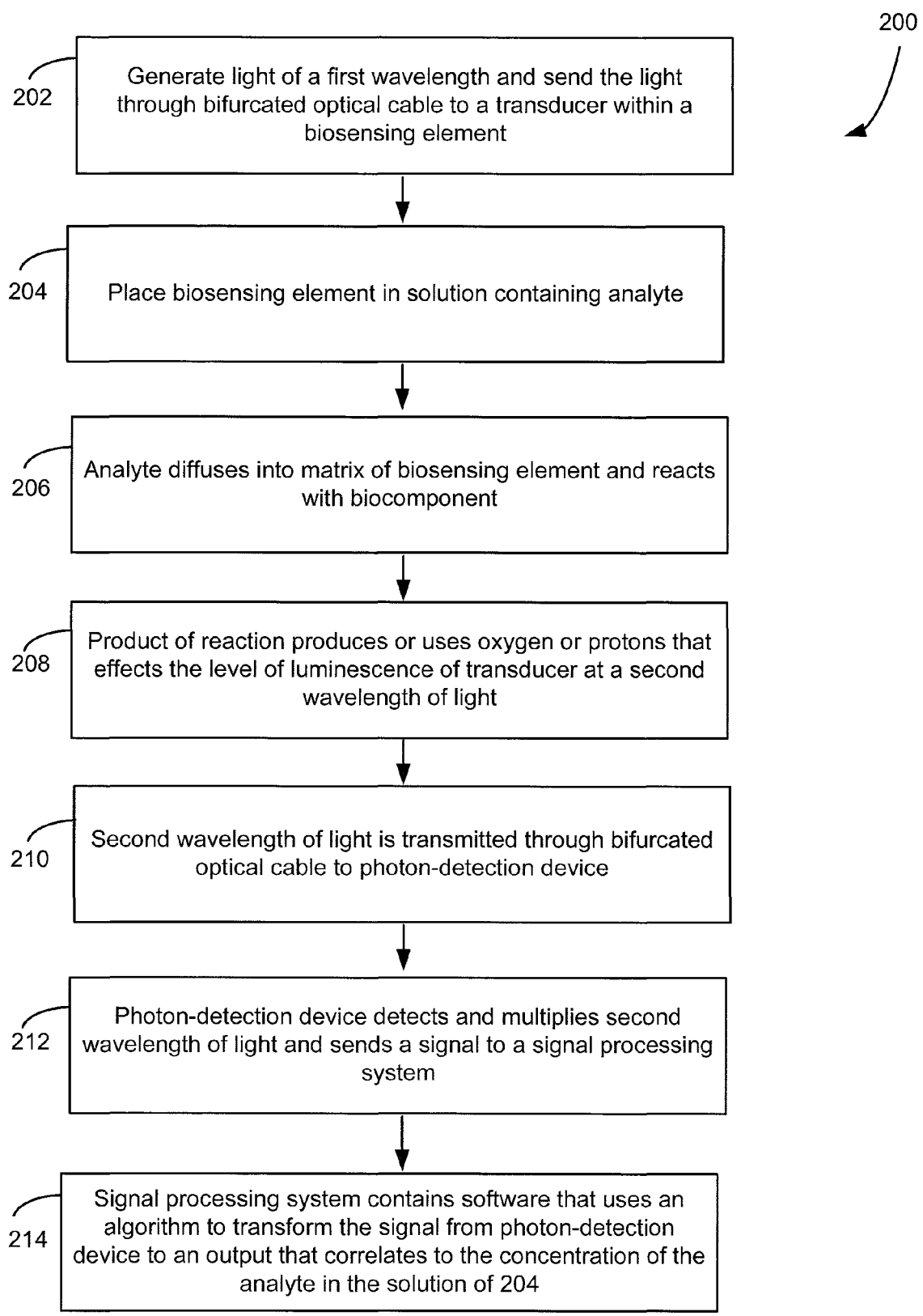
FIG. 10. Schematic representation of exemplary method for using a biosensing system to measure the concentration of an analyte in a solution.

FIG. 10 shows one exemplary method 200 for using a biosensing system to measure the concentration of an analyte in a solution. In step 202, method 200 is implemented by generating light of a first wavelength 82 by light source 70 as it passes through filter 80 and travels down bifurcated optical cable 50 to interact with transducer 30 of biosensing element 40. In step 204, method 200 is further implemented by placing biosensing element 40 at the end of a bifurcated optical cable 50 into a solution. In step 206, an analyte diffuses into matrix 22 and catalyzes the reaction of biocomponent 20. In step 208, the product of the reaction of the analyte with biocomponent 20 produces or uses oxygen and/or hydrogen ions that interact with transducer 30 to affect the amount of fluorescence at a second light wavelength 90 of transducer 30. In step 210, the second light wavelength 90 is transmitted through bifurcated optical cable 50 and detected by photon-detection device 60. In step 212, photon-detection device 60 detects and multiplies the signal of second light wavelength 90 and sends a signal to signal processing system 62. In step 214, signal processing system 62 has software 64 that uses an algorithm that transforms the signal from photon-detection device 60 into an output that can be read as a numerical representation of the concentration of the analyte in the solution that biosensing element 40 was placed into in step 204.

NAD(P)H Regenerating TOM Biosensing System

One embodiment of the regeneration of NADH using formate dehydrogenase is exemplified in Scheme 1. Scheme 1 depicts reactions within a NADH regeneration system comprising TOM and FDH. TOM catalyzes the reaction of toluene and oxygen while using NADH to generate 2-hydroxy toluene. FDH catalyzes the reaction of formate and NAD$^+$ to generate $CO_2$ and NADH which is then used in the TOM catalyzed reaction. Thus, scheme 1 depicts one embodiment of a cofactor regeneration system for use in biosensing systems.

Scheme 1:

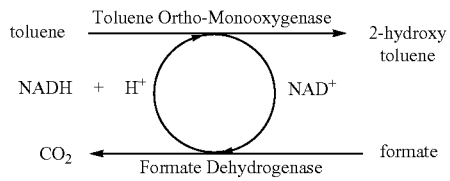

Biosensing systems made with *E. coli* cells expressing TOM only, or TOM and FDH, were constructed and tested three times each for their response to 92 µM toluene. After each test, the biosensing elements of the biosensing systems were placed in fresh measurement solution with formate (a solution of 0.15 M NaCl, 0.025 M $CaCl_2$, and 0.1 M sodium formate at pH 7.0) for 24 h. The control experiments were performed with three fresh TOM biosensing systems (n=3) that were only tested once each. The data in Table 1 demonstrate that the signal from biosensing systems made from cells containing both TOM and FDH was retained consistently over three consecutive measurements of toluene, whereas the signal from TOM only biosensing systems declined rapidly from one measurement to the next and was essentially at noise levels for the third measurement.

TABLE 1

Results of repeated measurements using toluene biosensing systems with and without FDH to enable NADH regeneration.

| | TOM | | | TOM + FDH | | |
|---|---|---|---|---|---|---|
| | Initial | Post-time | Signal | Initial | Post-time | Signal |
| Test 1 | 8750 | 9840 | 1090 | 9620 | 9940 | 320 |
| Test 2 | 11020 | 11470 | 450 | 9610 | 9910 | 300 |
| Test 3 | 9210 | 9230 | 20 | 9610 | 9900 | 290 |
| Control | Avg of signal = 1066, Std dev of signal = 29, n = 3 | | | | | |

Biosensing systems made with *E. coli* cells expressing TOM and FDH were constructed and tested at various time points and then stored in buffer with formate. This cycle was repeated. The results demonstrate that the biosensing systems with TOM and FDH retained activity when used over 2 weeks and had essentially the same activity after being used on and off over 2 weeks as cells that had been stored but not used, see FIG. 1.

Storage Lifetime

Figure 2:
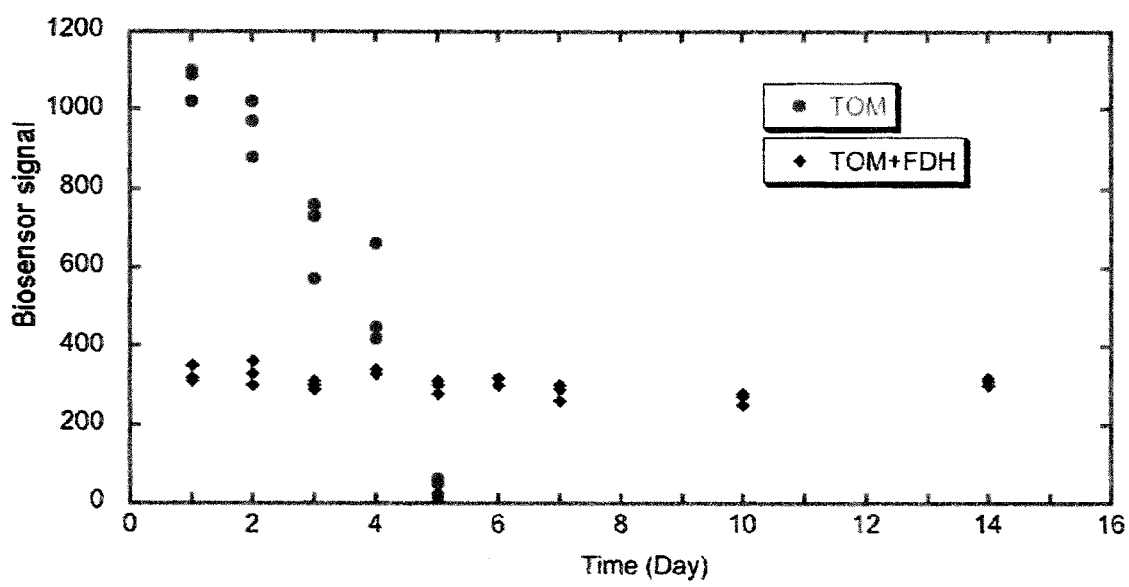
FIG. 2. Storage tests of toluene biosensing systems, comparing those without NADH recycling (TOM) to those with NADH recycling via formate/FDH.

Biosensing systems made with *E. coli* cells expressing TOM only, or TOM and FDH, were constructed. Each biosensing system was used only once, and all biosensing elements of the biosensing systems were stored at room temperature in a buffer solution with formate until they were tested. The results demonstrate that the biosensing systems made from cells with both TOM and FDH did not lose any activity over two weeks of storage, see FIG. 2.

EXAMPLES

The following examples are prophetic and are included as non-limiting illustrations of potential embodiments of the present disclosure.

Bacterial Strains and Growth Conditions

In one prophetic example, biosensing systems use various biocomponent enzymes such as toluene ortho monooxygenase, toluene ortho monooxygenase variants, formate dehydrogenase, epoxide hydrolase (EchA), γ-glutamylcysteine synthetase (GSHI). Combinations of the biocomponent enzymes include: TOM-Green/FDH, TOM/FDH, TOM-Green/FDH/EchA and TOM-Green/GSHI/FDH, all of which may be expressed in *E. coli* strain TG1. *E. coli* cultures can be grown aerobically on agar plates made from Luria-Bertani (LB) medium with 20 g/L Bacto-agar (Difco) and 100 mg/L kanamycin (and an additional selective antibiotic if required) at 30° C. for 24 h. A culture tube containing 2 mL LB medium supplemented with the same concentrations of antibiotics is then inoculated from an individual colony on an agar plate and shaken overnight at 30° C. and 200 rpm, then transferred to a flask containing 200 mL of the same LB-Kan medium and shaken at 30° C. and 200 rpm. The cell concentration is measured as culture absorbance at 600 nm (optical density at 600 nm, $OD_{600}$) with a spectrophotometer Spectronic® 20 Genesys™, Thermo Electron Corporation. IPTG solution is prepared with deionized water and added to the culture with a final concentration of 1 mM in the early exponential growth phase ($OD_{600}$ of 0.6) to induce cellular expression of plasmids. The culture is then harvested 4 h after IPTG is added, centrifuged, and resuspended in 20 mL of a solution containing 10 mM phosphate-buffered saline at pH 7.4 and stored at 4° C. until further use.

Exemplary Biosensing System

In one prophetic example, a biosensing system consisting of a layer of whole cells immobilized over an oxygen optode may be constructed from a 25-cm section of PMMA optical fiber terminated with an ST connector. The fiber jacket is detached from 1 mm of the distal end (non-connector terminated) and then polished with 2000-grit and 3 μm polishing film (part of a fiber optic tool kit, IF-TK4-RP2, Industrial Fiber Optics) to minimize potential signal loss due to scattering. One mg of the oxygen-sensitive RuDPP is then dissolved into 1 mL chloroform and mixed with 200 mg silicone gel (clear RTV silicone, Permatex, Inc.). A 1 μL aliquot of this mixture is then added to the polished fiber tip. The RuDPP gel layer is affixed to the optical fiber end as soon as the chloroform evaporated. Previously stored E. coli whole cells containing plasmids encoding enzymes TOM, TOM-Green, epoxide hydrolase, glutathione synthetase, glutathione S-transferase, and/or γ-glutamylcysteine sythetase, and FDH may then be centrifuged and mixed with sodium alginate solution (2.5% w/w) in a cell-to-alginate ratio (wet cell mass:alginate solution) of 1:1 w/w. A 2-μL aliquot of the cell-alginate mixture is then placed on the tip of each oxygen optode and immobilized after immersing the optode in 0.47 M calcium chloride solution for 30 min at 0° C. All biosensing elements can then be stored at 0° C. in a solution of 0.15 M NaCl and 0.025 M $CaCl_2$ at pH 7.0, the measurement solution.

Biosensing System Measurement Protocols

In one prophetic example, all biosensing system experiments are performed in 5 mL glass vials containing 4 mL of measurement solution saturated with air at room temperature with a small magnetic stir bar for rapid mixing. The biosensing element is then immersed in this solution, sealed in the glass vial with a rubber septum, and shielded from external light sources. Aliquots of 0.1 mL of a TCE solution of 0.1 to 4 mg/L are injected into the measurement solution after the biosensing system has produced a steady output. A steady output is defined as the time when the variation in the output is no larger than the peak-to-peak noise for a period of at least 5 min. All measurements are performed at room temperature unless temperature effects are to be studied. Each measurement is performed with a fresh biosensing element to distinguish the effect in question (e.g., temperature, pH, cell/alginate mass ratio). Biosensing elements should not be reused unless it is necessary.

Preparation of Biosensing Element Using Dry-Heated Cells

In another prophetic example, biocomponents of the biosensing element of the present disclosure are prepared by using dry-heated cells. In order to prepare dry heated cells, cells stored at 4° C. in phosphate-buffered saline solution may then be centrifuged at 15,000×g for 3 minutes and washed twice with distilled water. These cells may then be suspended in a small quantity of water (3 mL of stored cell suspension were washed and then suspended in 0.5 mL of water). This suspension is put in a 10-mL beaker and water is completely removed by vacuum drying at 35° C. It takes about an hour to dry these cells. The dried cells are then scratched off from the surface of beaker using a spatula. The beaker is then covered with aluminum foil and left in the oven at a constant temperature of 270° C. and for a given period of time (30 sec, 60 sec, etc.). These dry heated cells may look like a highly porous solid and have a light orange color. These dry-heated cells (~0.003-0.004 g) may also be immobilized using the same entrapment method. These cells are then directly mixed with 4% (w/v) of alginate, thus forming small bubbles in the cell-alginate mixture. Since it is important to eliminate these bubbles in order to obtain a stable response, these cells are first suspended in 10 μL of NaOH (pH 7.0) in a 1.5 mL-vial and then 8% (w/v) of alginate is added (from about 0.3 to about 0.5 g/g of dry wt. of cells to wt. of alginate). This mixture is used to make the biosensing element that is incorporated into the biosensing system.

Preparation of Biosensing Element Using Chloramphenicol Treated Cells

In one prophetic example, cells stored at 4° C. in phosphate-buffered saline are centrifuged at 15,000×g for 2 min and the pellet is then washed twice with saline (9 g/L of NaCl [pH 7.1]) containing 50 μg/mL of chloramphenicol. Next, sodium alginate (4% w/v in water) containing either 50 or 200 μg/mL of chloramphenicol is added and mixed well with the cell pellet. This cell and alginate mixture is kept for 5 minutes at room temperature before it is used to make the biosensing element.

Preparation of Biosensing Element Using Protease Inhibitor Treated Cells

In another prophetic example, cells stored at 4° C. in phosphate-buffered saline are centrifuged at 15,000×g for 2 min and the pellet is then washed twice with saline (9 g/L of NaCl [pH 7.1]) containing 5 μL of protease inhibitor cocktail in 1 mL of saline solution. This cocktail is prepared by adding 215 mg of lyophilized protease inhibitor in a solution containing 1 mL of DMSO (Dimethyl sulfoxide) and 4 mL of deionized water. The cocktail has a broad specificity for the inhibition of serine, cysteine, aspartic and metalloproteases, and aminopeptidases. It is stored at −20° C. in the freezer. These cells are then mixed with Na-alginate solution (4% w/v) containing 200 μL of cocktail per mL of alginate solution. The cell-alginate mixture is left for about 5 minutes at room temperature before it is used for making the biosensing element. The ratio of the weight of wet cells to the weight of alginate used in the experiment is 0.72 g/g.

In another prophetic example, purified enzymes may be used to prepare a biosensing element by substituting purified enzymes for whole cells in the prophetic example above.

Preparation of Biosensing Element With a Poly-L-Lysine Coating

In another prophetic example, the alginate bead is coated with poly-L-lysine (PLL) by preparing the biosensing element with a biocomponent as described above. The Ca-alginate bead on the biosensing element is then washed twice with saline solution (9 g/L of NaCl in water). Then the biosensing element is immersed in 10 mL of 0.4% (w/v) of poly-L-lysine.HCl solution, stored at 4° C. inside the refrigerator) in saline for 30 minutes at 30° C.

In one prophetic example, the PLL layer's thickness can be varied through multiple rounds of application of PLL in to create a diffusivity barrier to enable the biosensing element to respond linearly to the concentration of an analyte in a solution being measured by the biosensing system.

Construction of Biosensing System With Oxygen Sensitive Transducer Layer

In one prophetic example, a general method for constructing a biosensing element having an oxygen sensitive transducer layer is presented as follows. The optode used in the biosensing system is an oxygen optode. An oxygen optode is a biosensing system based on optical measurement of the oxygen concentration in a solution. In one embodiment, a chemical film is adhered to the tip of an optical cable and the fluorescent properties of this film depend on the oxygen concentration. Fluorescence is at a maximum when there is no oxygen present. When an $O_2$ molecule diffuses into the film it quenches the photoluminescence of the chemical film (transducer layer). For a given oxygen concentration there will be a specific number of $O_2$ molecules in the film at any given time, and the fluorescence properties will be stable.

In one prophetic example of a biosensing system that uses an oxygen optode, a biosensing system for measuring the concentration of an analyte consists of a layer of immobilized whole cells over an oxygen optode, which is constructed from a 25-cm section of PMMA optical fiber terminated with an ST connector. The fiber jacket is detached from 1 mm of the distal end (non-connector terminated) and then polished with 2000-grit and 3 µm polishing film (part of a fiber optic tool kit, IF-TK4-RP2, Industrial Fiber Optics) to minimize potential signal loss due to scattering. One mg of the oxygen-sensitive phosphorophore RuDPP, which may classified as a phosphorophore since it has longer decay lifetime than typical fluorophores, is dissolved into 1 mL chloroform and mixed with 200 mg silicone gel (clear RTV silicone, Permatex, Inc.). A 1-µL aliquot of this mixture is then added to the polished fiber tip. The RuDPP gel layer is affixed to the optical fiber end as soon as the chloroform evaporated. Previously stored *E. coli* whole cells (with plasmids which may encode for TOM, TOM-Green, epoxide hydrolase, glutathione synthetase, glutathione S-transferase, γ-glutamylcysteine sythetase, and/or FDH, for example) were centrifuged and mixed with sodium alginate solution (2.5%) in a cell-to-alginate ratio (wet cell mass:alginate solution) of 1:1 w/w unless otherwise specified. A 2 µL aliquot of the cell-alginate mixture is placed on the tip of each oxygen optode and immobilized after immersing the optode in 0.47 M calcium chloride solution for 30 min at 0° C. All biosensing elements are stored at 0° C. in a measurement solution of 0.15 M NaCl and 0.025 M $CaCl_2$ at pH 7.0.

Oxygen Based Biosensing System Instrumentation

In another prophetic example, an oxygen based biosensing system instrumentation consists of two separate optoelectronic modules: a 470 nm LED and a 450/60 nm optical bandpass filter (Chroma Technologies) as the excitation light source, and a computer-controlled Ocean Optics USB4000-FL spectrometer with 10 nm resolution for detection. The 470 nm excitation light is delivered through one leg of a bifurcated optical fiber assembly that has two 1 mm fibers side-by-side in the common end (Ocean Optics, Inc.), which is connected with the biosensing system via a ST connector. The phosphorescent emission light (peak at 620 nm) from the biosensing element is directed back into the detector through the other leg of the bifurcated optical fiber and measured by a spectrometer having a sensitivity of approximately 60 photons/count at 600 nm. The spectrometer output from 615 nm to 625 nm is integrated over 200 ms and five such values are averaged to yield one measurement value per second. The change in the intensity of the emission light over time correlates to the oxygen concentration change in the RuDPP layer of the biosensing element of the biosensing system.

Mitigation of Epoxide Toxicity and Cofactor Recycling

In one prophetic example, epoxide toxicity to the biocomponents is mitigated. During the reaction of oxygenases with their substrate molecules, highly reactive epoxide intermediates may be generated. These epoxide intermediates may react with active site residues of the biocomponent oxygenase enzyme or the dehydrogenase enzyme and thus cause the biocomponents to lose activity. In one example, the epoxide intermediate TCE epoxide is generated from the activity of TOM acting on TCE. *E. coli* cells with genes for TOM and/or TOM-Green, and genes for GSHI and/or EchA are developed and used to mitigate the damage created by TCE epoxide or other epoxides.

In one embodiment of the prophetic example, the combination of genes for TOM, GSHI, and FDH in *E. coli* enables retention of activity of the TOM biocomponent through both epoxide toxicity reduction (by GSHI) and cofactor recycling through the recycling of NADH using FDH as another biocomponent in the biosensing system. NADH recycling via an external supply of formate can replenish biocomponent TOM activity since intracellular FDH and/or FDH expressed from plasmids within the *E. coli* can reduce the NAD+ to NADH by the oxidation of formate.

In one prophetic example, formate is supplied to the FDH biocomponent via diffusion from a capillary tube containing a concentrated solution of formate. The capillary is positioned such that it delivers the formate at a constant rate within the matrix that the biocomponent is disposed within. In another embodiment, the formate is part of the matrix, immobilizing structure or other membrane or porous layer associated with the biosensing element and diffuses into the immobilized FDH where the formate is used as an electron donor in order to recycle NADP to NADPH. For example, a formate salt could be ionically associated with a matrix within which the biocomponents are immobilized such that when the biosensing element is exposed to the solution containing the analyte of interest, the formate salt would diffuse into the biocomponent containing FDH. The rate at which the formate salt dissolves and then diffuses into the biocomponent could be controlled through modifying the type of formate salt, the concentration of the formate salt, the amount of the formate salt, and the availability of the formate salt to water molecules from the solution and the size of the matrix cells in which the formate salt is associated with. In an additional embodiment of the prophetic example, an amount of formate salt could be encapsulated within a semi-permeable membrane or other porous layer that is itself immobilized within the same matrix that the biocomponents are immobilized within on the biosensing element portion of the biosensing system. The diffusion of the formate salt through the semi-permeable membrane or other porous layer could be controlled by selected an appropriate volume/surface area ratio of the formate salt to semi-permeable membrane/porous layer as well as controlling what the semi-permeable membrane or porous layer is made from.

The above examples, embodiments, definitions and explanations should not be taken as limiting the full metes and bounds of the invention.

REFERENCES

The contents of the following references are hereby incorporated into the present disclosure:

Chemical-market-reporter. CMR (1996).

D. J. Jollow, J. V. Bruckner, D. C. McMillan, J. W. Fisher, D. G. Hoel, L. C. Mohr. Critical Reviews in Toxicology 39, 782-797 (2009).

J. R. Burg, G. L. Gist. Archives of Environmental Health 54, 231-241 (1999).

C. S. Scott, W. A. Chiu. Environmental Health Perspectives 114, 1471-1478 (2006).

S. Tabrez, M. Ahmad. Journal of Environmental Science and Health Part C-Environmental Carcinogenesis & Ecotoxicology Reviews 27, 178-196 (2009).

L. P. Wackett, D. T. Gibson. Applied and Environmental Microbiology 54, 1703-1708 (1988).

D. Poli, P. Manini, R. Andreoli, I. Franchini, A. Mutti. Journal of Chromatography B—Analytical Technologies in the Biomedical and Life Sciences 820, 95-102 (2005).

M. Rosell, S. Lacorte, D. Barcelo. Journal of Chromatography A 1132, 28-38 (2006).

P. Williams, L. Benton, J. Warmerdam, P. Sheehan. Environmental Science & Technology 36, 4721-4728 (2002).

A. S. Bangalore, G. W. Small, R. J. Combs, R. B. Knapp, R. T. Kroutil, C. A. Traynor, J. D. Ko. Analytical Chemistry 69, 118-129 (1997).

S. T. Vohra, F. Bucholtz, G. M. Nau, K. J. Ewing, I. D. Aggarwal. Applied Spectroscopy 50, 985-990 (1996).

S. F. D'Souza. Biosensors & Bioelectronics 16, 337-353 (2001).

K. F. Reardon, Z. Zhong, K. L. Lear. In Optical Sensor Systems in Biotechnology, pp. 99-123. Springer-Verlag Berlin, Berlin (2009).

M. D. Rubianes, G. A. Rivas. Electroanalysis 17, 73-78 (2005).

D. W. Campbell, C. Muller, K. F. Reardon. Biotechnology Letters 28, 883-887 (2006).

D. J. Monk, D. R. Walt. Analytical and Bioanalytical Chemistry 379, 931-945 (2004).

O. S. Wolfbeis. Analytical Chemistry 74, 2663-2677 (2002).

M. S. Shields, M. J. Reagin, R. R. Gerger, R. Campbell, C. Somerville. Applied and Environmental Microbiology 61, 1352-1356 (1995).

K. A. Canada, S. Iwashita, H. Shim, T. K. Wood. Journal of Bacteriology 184, 344-349 (2002).

J. Lee, L. Cao, S. Y. Ow, M. E. Barrios-Llerena, W. Chen, T. K. Wood, P. C. Wright. Journal of Proteome Research 5, 1388-1397 (2006).

L. Y. Rui, K. F. Reardon, T. K. Wood. Applied Microbiology and Biotechnology 66, 422-429 (2005).

L. Y. Rui, Y. M. Kwon, K. F. Reardon, T. K. Wood. Environmental 27 Microbiology 6, 491-500 (2004).

S. B. Pieper, S. P. Mestas, K. L. Lear, Z. Zhong, K. F. Reardon. Applied Physics 2 Letters 92, 3 (2008).

O. Kohls. In Institut für Teschnische Chemie. Universität Hannover, Hannover (1995).

J. R. Lakowicz. Principles of Fluorescence Spectroscopy. Springer-Verlag, Berlin (2006).

B. M. Willardson, J. F. Wilkins, T. A. Rand, J. M. Schupp, K. K. Hill, P. Keim, P. J. Jackson. Applied and Environmental Microbiology 64, 1006-1012 (1998).

M. H. Chen, C. C. Liu, T. C. Chou. Biosensors & Bioelectronics 20, 25-32 (2004).

T. S. Han, S. Sasaki, K. Yano, K. Ikebukuro, A. Kitayama, T. Nagamune, I. Karube. Talanta 57, 271-276 (2002).

J. Vlieg, D. B. Janssen. Journal of Biotechnology 85, 81-102 (2001).

S. J. Berrios-Rivera, G. N. Bennett, K. Y. San. Metabolic Engineering 4, 217-229 (2002).

H. Slusarczyk, S. Felber, M. R. Kula, M. Pohl. European Journal of Biochemistry 267, 1280-1289 (2000).

Z. Zhong, M. Fritzsche, S. B. Pieper, T. K. Wood, Kevin L. Lear, D. S. Dandy, K. F. Reardon. Biosensors and Bioelectronics, In Press (2010).

K. Noda, H. Aizaiwa, S. Kurosawa. Sensors and Materials 20, 179-189 (2008).

Ikeda et al., J. Electroanal. Chem., 361, 221, (1993).

Safina et al., Electrochimica Acta, 55, 7690-7695(2010).

Roda A, Cevenini L, Michelini E, Branchini B R. A portable bioluminescence engineered cell-based biosensor for on-site applications. Biosens Bioelectron. 2011 Apr. 15; 26(8):3647-53.

Sezgintürk M K, Dinçkaya E. A Biosensor for the Determination of β-galactosidase Activity: A Different Viewpoint on Biosensors. Artif Cells Blood Substit Immobil Biotechnol. 2011 Feb. 25.

Sezgintürk M K, Dinçkaya E. β-galactosidase Determination by an Electrochemical Biosensor Mediated with Ferrocene. Artif Cells Blood Substit Immobil Biotechnol. 2011 Feb. 22.

Leal M P, Assali M, Fernández I, Khiar N. Copper-catalyzed azide-alkyne cycloaddition in the synthesis of polydiacetylene: "click glycoliposome" as biosensors for the specific detection of lectins. Chemistry. 2011 Feb. 7; 17(6):1828-36.

Veetil J V, Jin S, Ye K. A glucose sensor protein for continuous glucose monitoring. Biosens Bioelectron. 2010 Dec. 15; 26(4):1650-5.

Moreira F T, Kamel A H, Guerreiro J R, Sales M G. Man-tailored biomimetic sensor of molecularly imprinted materials for the potentiometric measurement of oxytetracycline. Biosens Bioelectron. 2010 Oct. 15; 26(2):566-74.

Yang C, Zhang Z, Shi Z, Xue P, Chang P, Yan R. Application of a novel co-enzyme reactor in chemiluminescence flow-through biosensor for determination of lactose. Talanta. 2010 Jun. 30; 82(1):319-24.

Ren X, Yang L, Tang F, Yan C, Ren J. Enzyme biosensor based on NAD-sensitive quantum dots. Biosens Bioelectron. 2010 Sep. 15; 26(1):271-4.

Conzuelo F, Gamella M, Campuzano S, Ruiz M A, Reviejo A J, Pingarrón J M. An integrated amperometric biosensor for the determination of lactose in milk and dairy products. J Agric Food Chem. 2010 Jun. 23; 58(12):7141-8.

Nagatsuka T, Uzawa H, Ohsawa I, Seto Y, Nishida Y. Use of lactose against the deadly biological toxin ricin. ACS Appl Mater Interfaces. 2010 April; 2(4):1081-5.

Kawsar S M, Matsumoto R, Fujii Y, Yasumitsu H, Dogasaki C, Hosono M, Nitta K, Hamako J, Matsui T, Kojima N, Ozeki Y. Purification and biochemical characterization of a D-galactose binding lectin from Japanese sea hare (*Aplysia kurodai*) eggs. Biochemistry (Mosc). 2009 July; 74(7):709-16.

Muñoz F J, Pérez J, Rumbero A, Santos J I, Cañada F J, André S, Gabius H J, Jiménez-Barbero J, Sinisterra J V, Hernáiz M J. Glycan tagging to produce bioactive ligands for a surface plasmon resonance study via immobilization on different surfaces. Bioconjug Chem. 2009 April; 20(4): 673-82.

Jenkins D M, Teruel M A, Reyes-de-Corcuera J I, Young O. Simultaneous determination of hydrolysis and mutarotation rates during the enzymatic hydrolysis of lactose. J Agric Food Chem. 2008 Sep. 24; 56(18):8303-8.

Sezgintürk M K, Dinçkaya E. Beta-galactosidase monitoring by a biosensor based on Clark electrode: its optimization, characterization and application. Biosens Bioelectron. 2008 Jul. 15; 23(12):1799-804.

Varshney M, Li Y. Double interdigitated array microelectrode-based impedance biosensor for detection of viable *Escherichia coli* O157:H7 in growth medium. Talanta. 2008 Jan. 15; 74(4):518-25.

Mora F, Tran D H, Oudry N, Hopfgartner G, Jeannerat D, Sakai N, Matile S. Interface engineering of synthetic pores: towards hypersensitive biosensors. Chemistry. 2008; 14(6):1947-53.

Seo J H, Adachi K, Lee B K, Kang D G, Kim Y K, Kim K R, Lee H Y, Kawai T, Cha H J. Facile and rapid direct gold surface immobilization with controlled orientation for carbohydrates. Bioconjug Chem. 2007 November-December; 18(6):2197-201.

Sharma S K, Kumar A, Chaudhary R, Suman, Pundir C S, Sehgal N. Lactose biosensor based on lactase and galactose oxidase immobilized in polyvinyl formal. Artif Cells Blood Substit Immobil Biotechnol. 2007; 35(4):421-30.

Betancor L, Luckarift H R, Seo J H, Brand O, Spain J C. Three-dimensional immobilization of beta-galactosidase on a silicon surface. Biotechnol Bioeng. 2008 Feb. 1; 99(2):261-7.

Stoica L, Ruzgas T, Ludwig R, Haltrich D, Gorton L. Direct electron transfer—a favorite electron route for cellobiose dehydrogenase (CDH) from *Trametes villosa*. Comparison with CDH from *Phanerochaete chrysosporium*. Langmuir. 2006 Dec. 5; 22(25): 10801-6.

Turishcheva G Kh, Kazarinov I A, Ignatov O V, Ignatov V V. [A bioelectrochemical study of a suspension of *Escherichia coli* cells metabolizing glucose and lactose]. Mikrobiologiia. 2006 January-February; 75(1):52-6. Russian.

Zhang Y, Luo S, Tang Y, Yu L, Hou K Y, Cheng J P, Zeng X, Wang P G. Carbohydrate-protein interactions by "clicked" carbohydrate self-assembled monolayers. Anal Chem. 2006 Mar. 15; 78(6):2001-8.

Stoica L, Ludwig R, Haltrich D, Gorton L. Third-generation biosensor for lactose based on newly discovered cellobiose dehydrogenase. Anal Chem. 2006 Jan. 15; 78(2):393-8.

Maestre E, Katakis I, Narváez A, Domínguez E. A multianalyte flow electrochemical cell: application to the simultaneous determination of carbohydrates based on bioelectrocatalytic detection. Biosens Bioelectron. 2005 Nov. 15; 21(5):774-81. PubMed PMID: 16242617.

Sharma S K, Singhal R, Malhotra B D, Sehgal N, Kumar A. Lactose biosensor based on Langmuir-Blodgett films of poly(3-hexyl thiophene). Biosens Bioelectron. 2004 Oct. 15; 20(3):651-7.

Jenkins D M, Delwiche M J. Adaptation of a manometric biosensor to measure glucose and lactose. Biosens Bioelectron. 2003 January; 18(1):101-7.

Rajendran V, Lrudayaraj J. Detection of glucose, galactose, and lactose in milk with a microdialysis-coupled flow injection amperometric sensor. J Dairy Sci. 2002 June; 85(6):1357-61.

Curey T E, Salazar M A, Oliveira P, Javier J, Dennis P J, Rao P, Shear J B. Enzyme-based sensor arrays for rapid characterization of complex disaccharide solutions. Anal Biochem. 2002 Apr. 1; 303(1):42-8.

Lehmann M, Riedel K, Adler K, Kunze G. Amperometric measurement of copper ions with a deputy substrate using a novel *Saccharomyces cerevisiae* sensor. Biosens Bioelectron. 2000 June; 15(3-4):211-9.

Ramakrishnan A, Sadana A. Analyte-receptor binding and dissociation kinetics for biosensor applications: a fractal analysis. Biosens Bioelectron. 2000; 15(11-12):651-62.

Eshkenazi I, Sacks V, Neufeld T, Rishpon J. Amperometric biosensors based on microflow injection system. Appl Biochem Biotechnol. 2000 November-December; 89(2-3):217-30.

Eshkenazi I, Maltz E, Zion B, Rishpon J. A three-cascaded-enzymes biosensor to determine lactose concentration in raw milk. J Dairy Sci. 2000 September; 83(9):1939-45.

Tkác J, Sturdík E, Gemeiner P. Novel glucose non-interference biosensor for lactose detection based on galactose oxidase-peroxidase with and without co-immobilised beta-galactosidase. Analyst. 2000 July; 125(7):1285-9.

Svitel J, Curilla O, Tkác J. Microbial cell-based biosensor for sensing glucose, sucrose or lactose. Biotechnol Appl Biochem. 1998 April; 27 (Pt 2):153-8.

Sorochinskii V V, Kurganov B I. [Biosensors for detecting organic compounds. II. Sensors for carbohydrates, aromatic, heterocyclic and other organic compounds]. Prikl Biokhim Mikrobiol. 1998 January-February; 34(1):22-42. Review. Russian.

Ruzgas T, Csöregi E, Katakis I, Kenausis G, Gorton L. Preliminary investigations of an amperometric oligosaccharide dehydrogenase-based electrode for the detection of glucose and some other low molecular weight saccharides. J Mol Recognit. 1996 September-December; 9(5-6):480-4.

Szabó E E, Adányi N, Váradi M. Application of biosensor for monitoring galactose content. Biosens Bioelectron. 1996; 11(10):1051-8.

Filipiak M, Fludra K, Gościmińska E. Enzymatic membranes for determination of some disaccharides by means of an oxygen electrode. Biosens Bioelectron. 1996; 11(4): 355-64.

Sriyudthsak M, Cholapranee T, Sawadsaringkarn M, Yupongchaey N, Jaiwang P. Enzyme-epoxy membrane based glucose analyzing system and medical applications. Biosens Bioelectron. 1996; 11(8):735-42.

Katsu T, Zhang X, Rechnitz G A. Simultaneous determination of lactose and glucose in milk using two working enzyme electrodes. Talanta. 1994 June; 41(6):843-8.

Carlsson H, Ljungcrantz P, Lindbladh C, Persson M, Billow L. Use of genetically prepared enzyme conjugates in lactose and galactose analyses. Anal Biochem. 1994 May 1; 218(2):278-83.

Kiefer H, Klee B, John E, Stierhof Y D, Jähnig F. Biosensors based on membrane transport proteins. Biosens Bioelectron. 1991; 6(3):233-7.

Svorc J, Miertus S, Barlíková A. Hybrid biosensor for the determination of lactose. Anal Chem. 1990 Aug. 1; 62(15):1628-31.

Pfeiffer D, Ralis E V, Makower A, Scheller F W. Amperometric bi-enzyme based biosensor for the detection of lactose-characterization and application. J Chem Technol Biotechnol. 1990; 49(3):255-65.

Heppel, L. A. and Porterfield, V. T. Enzymatic dehalogenation of certain brominated and chlorinated compounds. *J. Biol. Chem.* 176 (1948) 763-769.

Goldman, P., Milne, G. W. A. and Keister, D. B. Carbon-halogen bond cleavage. 3. Studies on bacterial halidohydrolases. *J. Biol. Chem.* 243 (1968) 428-434.

Motosugi, M., Esaki, N. and Soda, K. Preparation and properties of 2-halo acid dehalogenase from *Pseudomonas putida*. Agric. Biol. Chem. 46 (1982) 837-838.

Goldman, P. The enzymatic cleavage of the carbon-fluorine bond in fluoroacetate. *J. Biol. Chem.* 240 (1965) 3434-3438.

Goldman, P. and Milne, G. W. A. Carbon-fluorine bond cleavage. II. Studies on the mechanism of the defluorination of fluoroacetate. *J. Biol. Chem.* 241 (1966) 5557-5559.

Chopra, I. J. and Teco, G. N. C. Characteristics of inner ring (3 or 5) monodeiodination of 3,5-diiodothyronine in rat liver: evidence suggesting marked similarities of inner and outer ring deiodinases for iodothyronines. *Endocrinology* 110 (1982) 89-97.

Goswani, A., Leonard, J. L. and Rosenberg, I. N. Inhibition by coumadin anticoagulants of enzymatic outer ring monodeiodination of iodothyronines. *Biochem. Biophys. Res. Commun.* 104 (1982) 1231-1238.

Smallridge, R. C., Burman, K. D., Ward, K. E., Wartofsky, L., Dimond, R. C., Wright, F. D. and Lathan, K. R. 3',5'-Diiodothyronine to 3'-monoiodothyronine conversion in the fed and fasted rat: enzyme characteristics and evidence for two distinct 5'-deiodinases. *Endocrinology* 108 (1981) 2336-2345.

Keuning, S., Janssen, D. B. and Witholt, B. Purification and characterization of hydrolytic haloalkane dehalogenase from *Xanthobacter autotrophicus* GJ10. *J. Bacteriol.* 163 (1985) 635-639.

Scholtz, R., Leisinger, T., Suter, F. and Cook, A. M. Characterization of 1-chlorohexane halidohydrolase, a dehalogenase of wide substrate range from an *Arthrobacter* sp. *J. Bacteriol.* 169 (1987) 5016-5021.

Yokota, T., Omori, T. and Kodama, T. Purification and properties of haloalkane dehalogenase from *Corynebacterium* sp. strain m15-3. *J. Bacteriol.* 169 (1987) 4049-4054.

Muller, R., Thiele, J., Klages, U. and Lingens, F. Incorporation of [18O] water into 4-hydroxybenzoic acid in the reaction of 4-chlorobenzoate dehalogenase from *Pseudomonas* sp. CBS 3. *Biochem. Biophys. Res. Commun.* 124 (1984) 178-182.

Chang, K. H., Liang, P. H., Beck, W., Scholten, J. D., Dunaway-Mariano, D. Isolation and characterization of the three polypeptide components of 4-chlorobenzoate dehalogenase from *Pseudomonas* sp. strain CBS-3. *Biochemistry* 31 (1992) 5605-5610.

Crooks, G. P., Copley, S. D. Purification and characterization of 4-chlorobenzoyl CoA dehalogenase from *Arthrobacter* sp. strain 4-CB 1. *Biochemistry,* 33 (1994) 11645-11649.

de Souza, M. L., Wackett, L. P., Boundy-Mills, K. L., Mandelbaum, R. T. and Sadowsky, M. J. Cloning, characterization, and expression of a gene region from *Pseudomonas* sp. strain ADP involved in the dechlorination of atrazine. *Appl. Environ. Microbiol.* 61 (1995) 3373-3378.

de Souza, M. L., Sadowsky, M. J. and Wackett, L. P. Atrazine chlorohydrolase from *Pseudomonas* sp. strain ADP: gene sequence, enzyme purification, and protein characterization. *J. Bacteriol.* 178 (1996) 4894-4900.

Lipke, H. and Kearns, C. W. DDT dechlorinase. I. Isolation, chemical properties, and spectrophotometric assay. *J. Biol. Chem.* 234 (1959) 2123-2128.

Lipke, H. and Kearns, C. W. DDT dechlorinase. II. Substrate and cofactor specificity. *J. Biol. Chem.* 234 (1959) 2129-2132.

Moorefield, H. H. Purification of DDT-dehydrochlorinase from resistant houseflies. Contr. Boyce Thompson Inst. 18 (1956) 303-310.

Nagasawa, T., Ishii, T. and Yamada, H. Physiological comparison of D-cysteine desulfhydrase of *Escherichia coli* with 3-chloro-D-alanine dehydrochlorinase of *Pseudomonas putida* CR 1-1. *Arch. Microbiol.* 149 (1988) 413-416.

Yamada, H., Nagasawa, T., Ohkishi, H., Kawakami, B. and Tani, Y. Synthesis of D-cysteine from 3-chloro-D-alanine and hydrogen sulfide by 3-chloro-D-alanine hydrogen chloride-lyase (deaminating) of *Pseudomonas putida*. *Biochem. Biophys. Res. Commun.* 100 (1981) 1104-1110. [Medline UI: 81281807]

Kohler-Staub, D. and Leisinger, T. Dichloromethane dehalogenase of *Hyphomicrobium* sp. strain DM2. *J. Bacteriol.* 162 (1985) 676-681. [Medline UI: 85182487]

Moriguchi, M., Hoshino, S. and Hatanaka, S.-I. Dehalogenation and deamination of 1-2-amino-4-chloro-4-pentenoic acid by *Proteus mirabilis*. *Agric. Biol. Chem.* 51 (1987) 3295.

Kumagai, H., Suzuki, H., Shigematsu, H. and Tuchikura, T. S-Carboxymethylcysteine synthase from *Escherichia coli*. *Agric. Biol. Chem.* 53 (1989) 2481-2487.

Hayaishi, O. Direct oxygenation by $O_2$, oxygenases. In: Boyer, P. D., Lardy, H. and Myrbäck, K. (Eds.), *The Enzymes,* 2nd ed., vol. 8, Academic Press, New York, 1963, p. 353-371.

Junker, F., Field, J. A., Bangerter, F., Ramsteiner, K., Kohler, H.-P., Joannou, C. L., Mason, J. R., Leisinger, T. and Cook, A. M. Dioxygenation and spontaneous deamination of 2-aminobenzene sulphonic acid in *Alcaligenes* sp. strain O-1 with subsequent meta ring cleavage and spontaneous desulphonation to 2-hydroxymuconic acid. *Biochem. J.* 300 (1994) 429-436.

Fujisawa, H. and Hayaishi, O. Protocatechuate 3,4-dioxygenase. I. Crystallization and characterization. *J. Biol. Chem.* 243 (1968) 2673-2681.

Adachi, K., Iwayama, Y., Tanioka, H. and Takeda, Y. Purification and properties of homogentisate oxygenase from *Pseudomonas fluorescens*. *Biochim. Biophys. Acta* 118 (1966) 88-97.

Hayaishi, O. and Sutton, W. B. Enzymatic oxygen fixation into acetate concomitant with the enzymatic decarboxylation of L-lactate. *J. Am. Chem. Soc.* 79 (1957) 4809-4810.

Renganathan, V. Possible involvement of toluene-2,3-dioxygenase in defluorination of 3-fluoro-substituted benzenes by toluene-degrading *Pseudomonas* sp. strain T-12. *Appl. Exp. Microbiol.* 55 (1989) 330-334.

Ensley, B. D. and Gibson, D. T. Naphthalene dioxygenase: purification and properties of a terminal oxygenase component. *J. Bacteriol.* 155 (1983) 505-511.

Fetzner, S., Mueller, R. and Lingens, F. Degradation of 2-chlorobenzoate by *Pseudomonas cepacia* 2CBS. *Biol. Chem. Hoppe-Seyler* 370 (1989) 1173-1182.

Suzuki, K., Takemori, S. and Katagiri, M. Mechanism of the salicylate hydroxylase reaction. IV. Fluorimetric analysis of the complex formation. *Biochim. Biophys. Acta* 191 (1969) 77-85.

Hosokawa, K. and Stanier, R. Y. Crystallization and properties of p-hydroxybenzoate hydroxylase from *Pseudomonas putida*. *J. Biol. Chem.* 241 (1966) 2453-2460.

Nakagawa, H. and Takeda, Y. Phenol hydroxylase. *Biochim. Biophys. Acta* 62 (1962) 423-426.

Ziegler, D. M. and Pettit, F. H. Microsomal oxidases. I. The isolation and dialkylarylamine oxygenase activity of pork liver microsomes. *Biochemistry* 5 (1966) 2932-2938.

Colby, J. Stirling, D. I. and Dalton, H. The soluble methane mono-oxygenase of *Methylococcus capsulatus* (Bath). Its ability to oxygenate n-alkanes, n-alkenes, ethers, and alicyclic, aromatic and heterocyclic compounds. *Biochem. J.* 165 (1977) 395-402.

Schenk, T., Müller, R., Mörsberger, F., Otto, M. K. and Lingens, F. Enzymatic dehalogenation of pentachlorophenol by extracts from *Arthrobacter* sp. strain ATCC 33790. *J. Bacteriol.* 171 (1989) 5487-5491.

Cardini, G. and Jurtshuk, P. The enzymatic hydroxylation of n-octane by *Corynebacterium* sp. strain 7E1C. *J. Biol. Chem.* 245 (1970) 2789-2796.

Augusteyn, R. C., de Jersey, J., Webb, E. C. and Zerner, B. On the homology of the active-site peptides of liver carboxylesterases. *Biochim. Biophys. Acta* 171 (1969) 128-137.

Dodgson, K. S., Spencer, B. and Williams, K. Studies on sulphatases. 13. The hydrolysis of substituted phenyl sulphates by the arylsulphatase of *Alcaligenes metacaligenes. Biochem. J.* 64 (1956) 216-221.

Aldridge, W. N. Serum esterases. I. Two types of esterase (A and B) hydrolysing p-nitrophenyl acetate, propionate and butyrate and a method for their determination. *Biochem. J.* 53 (1953) 110-117.

Augustinsson, K.-B. and Heimburger, G. Enzymatic hydrolysis of organophosphorus compounds. I. Occurrence of enzymes hydrolysing dimethyl-amido-ethoxy-phosphoryl cyanide (Tabun). *Acta Chem. Scand.* 8 (1954) 753-761.

Cardy, D. L. N., V. Laidler, G. P. C. Salmond, and J. C. Murrell, "Molecular Analysis of the Methane Monooxygenase (MMO) Gene Cluster of *Methylosinus trichosporium* OB3b," *Molecular Microbiology,* 1991. 5(2): pp. 335-342.

Stainthorpe, A. C., V. Lees, G. P. C. Salmond, H. Dalton, and J. C. Murrell, "The Methane Monooxygenase Gene Cluster of *Methylococcus capsulatus* (Bath)," *Gene,* 1990. 91: pp. 27-34.

Rosenzwieg, A. C., P. Nordlund, P. M. Takahara, C. A. Frederick, and S. J. Lippard, "Geometry of the Soluble Methane Monooxygenase Catalytic Diiron Center in Two Oxidation States," *Chemistry and Biology,* 1995. 2(6): pp. 409-418.

Shields, M. S. and S. C. Francesconi, Microbial Degradation of Trichloroethylene, Dichloroethylene, and Aromatic Pollutants, in U.S. Pat. No. 5,543,317. 1996.

Bertoni, G., F. Bolognese, E. Galli, and P. Barbieri, "Cloning of the Genes for and Characterization of the Early Stages of Toluene and o-Xylene Catabolism in *Pseudomonas stutzeri* OX1," *Applied and Environmental Microbiology,* 1996, 62(10): pp. 3704-3711

Bertoni, G., M. Martino, E. Galli, and P. Barbieri, "Analysis of the Gene Cluster Encoding Toluene/o-Xylene Monooxygenase from *Pseudomonas stutzeri* OX1," *Applied and Environmental Microbiology,* 1998. 64(10): pp. 3626-3632.

Pikus, J. D., J. M. Studts, C. Achim, K. E. Kauffmann, E. Munck, R. J. Steffan, K. McClay, and B. G. Fox, "Recombinant Toluene-4-Monooxygenase: Catalytic and Mossbauer Studies of the Purified Diiron and Rieski Components of a Four-Protein Complex," *Biochemistry,* 1996. 35: pp. 9106-9119; Yen, K.-M., "Construction of Cloning Cartridges for Development of Expression Vectors in Gram-Negative Bacteria," *J. Bacteriol.,* 1991. 173(17): pp. 5328-5335.

Newman, 1995; McClay, K., B. G. Fox, and R. J. Steffan, "Chloroform Mineralization by Toluene-Oxidizing Bacteria," *Applied and Environmental Microbiology,* 1996. 62(8): pp. 2716-2722.

Byrne, A. M., J. J. Kukor, and R. H. Olsen, "Sequence Analysis of the Gene Cluster Encoding Toluene-3-monooxygenase from *Pseudomonas pickettii* PK01," *Gene,* 1995. 154: pp. 65-70.

Nordlund, I., J. Powlowski, and V. Shingler, "Complete nucleotide sequence and polypeptide analysis of multicomponent phenol hydroxylase from *Pseudomonas* sp. strain CF600," *Journal of Bacteriology,* 1990. 172: pp. 6826-6833.

Stoica, L. and Ludwig, R. and Haltrich, D. and Gorton, L., Third-generation biosensor for lactose based on newly discovered cellobiose dehydrogenase, Analytical chemistry, vol. 78, no. 2, pp. 393-398, 2006.

Sharma, S. K. and Singhal, R. and Malhotra, B D and Sehgal, N. and Kumar, A., Lactose biosensor based on Langmuir-Blodgett films of poly 3-hexyl thiophene, Biosensors and Bioelectronics, vol. 20, no. 3, pp. 651-657, 2004.

Ferreira, L S and Trierweiler, J O and De Souza Jr, M B and Folly, R O M, A lactose fia-biosensor system for monitoring and process control, Brazilian Journal of Chemical Engineering, vol. 21, no. 2, pp. 307-315, 2004.

Marrakchi, M. and Dzyadevych, S. V. and Lagarde, F. and Martelet, C. and Jaffrezic-Renault, N., Conductometric biosensor based on glucose oxidase and beta-galactosidase for specific lactose determination in milk, Materials Science and Engineering: C, vol. 28, nos. 5-6, pp. 872-875, 2008.

Eshkenazi, I. and Maltz, E. and Zion, B. and Rishpon, J., A Three-Cascaded-Enzymes Biosensor to Determine Lactose Concentration in Raw Milk, Journal of dairy science, vol. 83, no. 9, pp. 1939-1945, 2000.

Liu, H. and Li, H. and Ying, T. and Sun, K. and Qin, Y. and Qi, D., Amperometric biosensor sensitive to glucose and lactose based on co-immobilization of ferrocene, glucose oxidase, beta-galactosidase and mutarotase in beta-cyclodextrin polymer, Analytica Chimica Acta, vol. 358, no. 2, pp. 137-144, 1998.

Tkac, J. and Sturdik, E. and Gemeiner, P., Novel glucose non-interference biosensor for lactose detection based on galactose oxidase-peroxidase with and without co-immobilised [small beta]-galactosidase, Analyst, vol. 125, no. 7, pp. 1285-1289, 2000.

Svorc, J. and Miertus, S. and Barlikova, A., Hybrid biosensor for the determination of lactose, Analytical chemistry, vol. 62, no. 15, pp. 1628-1631, 1990.

Pfeiffer, D. and Ralis, E. V. and Makower, A. and Scheller, F. W., Amperometric Bi-enzyme based biosensor for the detection of lactose—characterization and application, Journal of Chemical Technology and Biotechnology, vol. 49, no. 3, pp. 255-265, 1990.

Pilloton, R. and Mascini, M., Flow analysis of lactose and glucose in milk with an improved electrochemical biosensor, Food chemistry, vol. 36, no. 3, pp. 213-222, 1990.

Jenkins, D. M. and Delwiche, M. J., Adaptation of a manometric biosensor to measure glucose and lactose, Biosensors and Bioelectronics, vol. 18, no. 1, pp. 101-107, 2003.

Frreira, L S and Souza Jr, M B and Trierweiler, J O and Hitzmann, B. and Folly, R O M, Analysis of experimental biosensor/FIA lactose measurements, Brazilian Journal of Chemical Engineering, vol. 20, no. 1, pp. 7-13, 2003.

Ottenbacher, D. and Jahnig, F. and Gopel, W., A prototype biosensor based on transport proteins: Electrical transducers applied to lactose permease, Sensors and Actuators B: Chemical, vol. 13, nos. 1-3, pp. 173-175, 1993.

Loechel, C. and Chemnitius, G. C. and Borchardt, M. and Cammann, K., Amperometric bi-enzyme based biosensor for the determination of lactose with an extended linear range, Zeitschrift Lebensmitteluntersuchung und-Forschung A., vol. 207, no. 5, pp. 381-385, 1998.

Goktug, T. and Sezginturk, M. K. and Dinckaya, E., Glucose oxidase-[beta]-galactosidase hybrid biosensor based on glassy carbon electrode modified with mercury for lactose determination, Analytica chimica acta, vol. 551, nos. 1-2, pp. 51-56, 2005.

Yang, W. and Pang, P. and Gao, X. and Cai, Q. and Zeng, K. and Grimes, C. A., Detection of lactose in milk samples using a wireless multi-enzyme biosensor, Sensor Letters, vol. 5, no. 2, pp. 405-410, 2007.

Jturdk, E. and Gemeiner, P., Novel glucose non-interference biosensor for lactose detection based on galactose oxidase-peroxidase with and without co-immobilised beta-galactosidase, Analyst, vol. 125, no. 7, pp. 1285-1289, 2000

Louren, R J M and Serralheiro, M L M and Rebelo, M J F, Development of a new amperometric biosensor for lactose determination, Portugaliae Electrochimica Acta, vol. 21, no. 2, pp. 171-177, 2003.

Pyeshkova, V M and Saiapina, O Y and Soldatkin, O O and Kukla, O L and Dzyadevych, S V, Enzyme conductometric biosensor for determination of lactose, Biotechnology, pp. 76-84, 2008

Fritzen, M. and Schuhmann, W. and Lengeier, J W and Schmidt, H. L., Immobilized transport mutants of bacterial cells in biosensor arrays. Improved selectivity for the simultaneous determination of glucose and lactose, Progress in Biotechnology, vol. 11, pp. 821-827, 1996.

Svitel, J. and Curilla, O. and Tkac, J., Microbial cell-based biosensor for sensing glucose, sucrose or lactose, Biotechnology and applied biochemistry, vol. 27, no. 2, pp. 153-158, 1998.

Lu, E. and Sungur, S. and Yildiz, Y., Development of lactose biosensor based on beta-galactosidase and glucose oxidase immobilized into gelatin, Journal of Macromolecular Science, Part A, vol. 43, no. 3, pp. 525-533, 2006.

Lu, E. and Sungur, S. and Yildiz, Y., Development of Lactose Biosensor Based on Galactosidase and Glucose Oxidase Immobilized into Gelatin, Journal of Macromolecular Science-Part A: Pure and Applied Chemistry, vol. 43, no. 3, pp. 525-534, 2006.

Tkac, J. and Sturdik, E. and Gemeiner, P., Full Papers-Sensors-Novel glucose non-interference biosensor for lactose detection based on galactose oxidase-peroxidase with and without co-immobilised b-galactosidase, Analyst-Letchworth, 125, no. 7, 1285-1290, 2000.

Yang, C. and Zhang, Z. and Shi, Z. and Xue, P. and Chang, P. and Yan, R., Application of a novel co-enzyme reactor in chemiluminescence flow-through biosensor for determination of lactose, Talanta, 82, no. 1, 319-324, 2010.

Tkac, J. and Svitel, J., Bulletin Potravinarskeho Vyskumu (Slovak Republic); Determination of glucose and lactose in milk by a microbial biosensor; Stanovenie glukozy a laktozy v mlieku mikrobialnym sensorom, Bulletin of Food Research, 1997.

Park, I S and Kim, J H and Noh, B S and Kim, T J, Simultaneous determination of lactose and lactic acid in yoghurt by biosensor using dual cathode electrode, Korean Journal of Biotechnology and Bioengineering, Korea Republic, 1997.

C. Müller, F. Schubert and T. Scheper, Multicomponent fiberoptical biosensor for use in hemodialysis monitoring, SPIE Proc., Vol. 2131, pp. 555-562, Biomedical Fiber Optic Instrumentation, Los Angeles, Calif., USA, 1994.

Liu, H. and Ying, T. and Sun, K. and Li, H. and Qi, D., Reagentless amperometric biosensors highly sensitive to hydrogen peroxide, glucose and lactose based on N-methyl phenazine methosulfate incorporated in a Nafion film as an electron transfer mediator between horseradish peroxidase and an electrode, Analytica chimica acta, vol. 344, no. 3, pp. 187-199, 1997F.

Scheller, F. Schubert, Biosensoren. 1989, Berlin: Akademieverlag.

T. Scheper, K. F. Reardon, Sensors in Biotechnology, in Sensors, J. N. Zemel, Editor. 1992, VCH Verlaggesellschaft: Weinheim.

J. Sipior, L. Randers-Eichhorn, J. R. Lakowicz, G. M. Carter, G. Rao, Phase Fluorimetric Optical Carbon Dioxide Gas Sensor for Fermentation Off-Gas Monitoring, Biotechnol. Prog. 1996, 12, 266-271.

T. E. Barber, W. G. Fisher, E. A. Wachter, On-Line Monitoring of Aromatic Hydrocarbons Using a near-Ultraviolet Fiber-Optic Absorption Sensor, Environ. Sci. Technol. 1995, 29, 1576-1580.

H. Gutfreund, An Introduction to the Study of Enzymes. 1965, New York: J. Wiley.

The invention claimed is:

1. A biosensing system that measures the concentration of an analyte in a solution, said biosensing system comprising
a first biocomponent that catalyzes the reaction of said analyte and oxygen and uses a cofactor selected from the group consisting of NADH, NADPH, FADH, $FADH_2$, FMNH, $FMNH_2$, and
a second biocomponent that catalyzes the reaction of a cofactor selected from the group consisting of $NAD^+$, $NADP^+$, FADH, FMNH, FAD and FMN, and an electron donor, and
wherein said first biocomponent and said second biocomponent are immobilized within a matrix, and
wherein said matrix is in contact with a transducer layer, and
wherein said transducer layer is part of an optode.

2. The biosensing system of claim 1 wherein said transducer layer is an optical transducer that constitutively fluoresces and wherein the fluorescence is quenched during use by oxygen in an oxygen-containing solution.

3. The biosensing system of claim 1 wherein said first biocomponent is selected from the group consisting of monooxygenases and dioxygenases.

4. The biosensing system of claim 1 wherein said second biocomponent is formate dehydrogenase and said electron donor is formate.

5. The biosensing system of claim 1 further comprising a tip of a capillary tube, wherein said capillary tube contains formic acid or a salt of formate anion, such that formate is delivered through capillary action to said first and second biocomponent.

6. The biosensing system of claim 1, wherein
said analyte is a reactant in a reaction catalyzed by of an oxygenase enzyme, said oxygenase enzyme selected from the group consisting of Enzyme Commission numbers 1.13 and 1.14, and
wherein said oxygenase enzyme requires a reduced cofactor selected from the group consisting of NADH, NADPH, FADH, $FADH_2$, FMNH, and $FMNH_2$, and
wherein said first biocomponent comprises said oxygenase enzyme, and
wherein said second biocomponent comprises a dehydrogenase enzyme that catalyzes the reaction of an oxidized cofactor selected from the group consisting of $NAD^+$, $NADP^+$, FADH, FMNH, FAD and FMN and an electron donor, and
wherein a third biocomponent comprises an enzyme selected from the group consisting of epoxide hydrolase, glutathione synthetase, glutathione S-transferase and gamma-glutamylcysteine sythetase, and
wherein said first biocomponent catalyzes the reaction of said analyte and said cofactor selected from the group consisting of NADH, NADPH, FADH, $FADH_2$, FMNH, and FMNH$_2$ while consuming oxygen and producing oxidized cofactor and an epoxide product, and wherein said oxidized cofactor is reduced by said second biocomponent and said electron donor, and wherein said epoxide product is a reactant in the reaction catalyzed by said third biocomponent, and wherein a transducer layer fluoresces photons, and wherein oxygen quenches at least some of the fluorescent photons, and wherein said photons enter into a fiber optic cable and are transmitted to a photomultiplier, and wherein said photomultiplier produces an output signal that is coupled to an algorithm that transforms the signal generated by said photomultiplier into an output correlated to the concentration of said analyte in said solution.

7. The biosensing system of claim 6 wherein said first biocomponent is toluene ortho-monooxygenase.

8. The biosensing system of claim 6 wherein said first biocomponent is toluene ortho-monooxygenase-Green.

9. The biosensing system of claim 6 wherein said second biocomponent is formate dehydrogenase and said electron donor is formate.

10. The biosensing system of claim 1, wherein said optode comprises a fiber optical cable having a first tip and a second tip, and said first tip is covered by said transducer layer, and said transducer layer is covered by a biocomponent layer comprising said first and second biocomponent within said matrix, and said biocomponent layer is covered by a porous layer, and said second tip is coupled to a photon-detection device, and said photon-detection device is coupled to a signal processing system, and said analyte concentration in said solution, the depth of the biocomponent layer, the depth of the porous layer, the diffusion coefficient of said porous layer, the $K_m$ and $V_{max}$ of the reaction between said biocomponent and said analyte are selected such that the quotient between $Da^e$ and $4\beta$ is from about 10 to about 1000.

11. The biosensing system of claim 10 wherein said biocomponent layer comprises toluene ortho-monooxygenase, toluene ortho-monooxygenase-Green, or toluene ortho-monooxygenase Green and formate dehydrogenase.

12. The biosensing system of claim 10 wherein said biocomponent comprises toluene ortho-monooxygenase-Green, formate dehydrogenase and at least one enzyme selected from the group consisting of epoxide hydrolase, glutathione synthetase, glutathione S-transferase and gamma-glutamylcysteine sythetase.

13. The biosensing system of claim 10 wherein said transducer layer comprises RuDPP.

14. The biosensing system of claim 10 wherein said porous layer is track-etched polycarbonate.

15. The biosensing system of claim 1 wherein said first biocomponent and said second biocomponent are within or on the surface of a whole cell biocomponent that is immobilized within a matrix, and wherein said matrix is adhered to said transducer layer.

16. A method for measuring the concentration of an analyte in a solution using a biosensing system wherein said biosensing system comprises biocomponents, and wherein a first biocomponent of said biosensing system is an oxygenase enzyme that catalyzes a reaction that uses oxygen, said analyte and a reduced cofactor as reactants and produces oxidized cofactor, and wherein a second biocomponent of said biosensing system is a dehydrogenase enzyme that catalyzes a reaction that uses said oxidized cofactor and an electron donor as reactants and produces said reduced cofactor, and wherein said reduced cofactor is used in the reaction catalyzed by said first biocomponent, and wherein the oxygen concentration in said solution is measured by said biosensing system, and wherein the measured oxygen concentration in said solution is used to calculate the measurement of the concentration of said analyte in said solution.

17. The method of claim 16 wherein said biosensing system further comprises a transducer layer that fluoresces photons, and wherein oxygen quenches the emission of at least some of the fluorescent photons, and wherein said photons enter into a fiber optic cable and are transmitted to a photomultiplier, and wherein said photomultiplier produces an output signal that is coupled to an algorithm that transforms the signal generated by said photomultiplier into an output correlated to the concentration of said analyte in said solution.

18. The method of claim 16 wherein said first biocomponent is toluene ortho-monooxygenase or toluene ortho-monooxygenase-Green; and said second biocomponent is formate dehydrogenase and said electron donor is formate.

19. The method of claim 16 wherein said analyte is a reactant in the reaction catalyzed by an oxygenase enzyme, and wherein said oxygenase enzyme requires a cofactor selected from the group consisting of NADH, NADPH, FADH, FADH$_2$, FMNH, FMNH$_2$, and wherein said second biocomponent comprises a dehydrogenase enzyme that catalyzes the reaction of an oxidized cofactor selected from the group consisting of NAD$^+$, NADP$^+$, FADH, FMNH, FAD and FMN, and an electron donor, and wherein a third biocomponent comprises an enzyme selected from the group consisting of epoxide hydrolase, glutathione synthetase, glutathione S-transferase and gamma-glutamylcysteine sythetase, and wherein said first biocomponent catalyzes the reaction of said analyte and said cofactor selected from the group consisting of NADH, NADPH, FADH, FADH$_2$, FMNH, FMNH$_2$, while consuming oxygen and producing oxidized cofactor and an epoxide product, and wherein said oxidized cofactor is reduced by said second biocomponent and said electron donor, and wherein said epoxide product is a reactant in the reaction catalyzed by said third biocomponent, and wherein a transducer layer fluoresces photons, and wherein oxygen quenches the emission of at least some of the fluorescent photons, and wherein said photons enter into a fiber optic cable and are transmitted to a photomultiplier, and wherein said photomultiplier produces an output signal that is coupled to an algorithm that transforms the signal generated by said photomultiplier into an output correlated to the concentration of said analyte in said solution.

* * * * *